(12) United States Patent
Popel et al.

(10) Patent No.: US 11,981,754 B2
(45) Date of Patent: *May 14, 2024

(54) BIOMIMETIC PEPTIDE AND BIODEGRADABLE DELIVERY PLATFORM FOR THE TREATMENT OF ANGIOGENESIS- AND LYMPHANGIOGENESIS-DEPENDENT DISEASES

(71) Applicant: THE JOHNS HOPKINS UNIVERSITY, Baltimore, MD (US)

(72) Inventors: Aleksander S. Popel, Lutherville-Timonium, MD (US); Niranjan B. Pandey, White Marsh, MD (US); Esak Lee, Windsor Mill, MD (US); Jordan J. Green, Nottingham, MD (US); Ron B. Shmueli, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 795 days.

This patent is subject to a terminal disclaimer.

(21) Appl. No.: 16/989,416

(22) Filed: Aug. 10, 2020

(65) Prior Publication Data

US 2020/0361993 A1 Nov. 19, 2020

Related U.S. Application Data

(63) Continuation of application No. 15/712,890, filed on Sep. 22, 2017, now Pat. No. 10,774,112, which is a continuation of application No. 14/896,521, filed as application No. PCT/US2014/041526 on Jun. 9, 2014, now Pat. No. 9,802,984.

(60) Provisional application No. 61/832,290, filed on Jun. 7, 2013.

(51) Int. Cl.
| | |
|---|---|
| *C07K 7/08* | (2006.01) |
| *A61K 38/10* | (2006.01) |
| *A61K 45/06* | (2006.01) |
| *B82Y 5/00* | (2011.01) |
| *C12N 15/88* | (2006.01) |

(52) U.S. Cl.
CPC .............. *C07K 7/08* (2013.01); *A61K 38/10* (2013.01); *A61K 45/06* (2013.01); *B82Y 5/00* (2013.01); *C12N 15/88* (2013.01); *C12N 2510/00* (2013.01)

(58) Field of Classification Search
CPC .......... C07K 7/08; A61K 38/10; A61K 45/06; B82Y 5/00; C12N 15/88; C12N 2510/00; A61P 3/04; A61P 9/00; A61P 27/06; A61P 37/06; A61P 27/02; A61P 35/00; A61P 35/04; A61P 43/00
See application file for complete search history.

(56) References Cited

U.S. PATENT DOCUMENTS

| | | | |
|---|---|---|---|
| 2011/0028395 A1* | 2/2011 | Popel | C07K 14/00 |
| | | | 435/375 |
| 2011/0059167 A1 | 3/2011 | Fidanboylu et al. | |
| 2011/0206760 A1 | 8/2011 | Kliger et al. | |
| 2012/0114759 A1 | 5/2012 | Green et al. | |
| 2012/0232012 A1 | 9/2012 | Popel et al. | |
| 2012/0270770 A1 | 10/2012 | Jaynes | |

FOREIGN PATENT DOCUMENTS

| | | |
|---|---|---|
| JP | 2013514977 A | 2/2011 |
| WO | 2007116278 | 10/2007 |
| WO | 2011084620 A2 | 7/2011 |
| WO | 2012079088 | 6/2012 |

OTHER PUBLICATIONS

Abraham S, Guo F, Li LS, Rader C, Liu C, Barbas CF, 3rd, et al. (2007) Synthesis of the next generation therapeutic antibodies that combine cell targeting and antibody-catalyzed prodrug activation. Proc Natl Acad Sci; 104: 5584-9.

Arnaoutova I, George J, Kleinman HK, Benton G (2009) The endothelial cell tube formation assay on basement Membrane turns 20: state of the science and the art. Angiogenesis; 12: 267-74.

Avraamides, C. J.; Garmy-Susini, B.; Varner, J. A. Integrins in angiogenesis and lymphangiogenesis. Nat. Rev. Cancer 2008, 8(8), 604-617.

Bhujwalla ZM, Artemov D, Natarajan K, Ackerstaff E, Solaiyappan M. Vascular differences detected by MRI for metastatic versus nonmetastatic breast and prostate cancer xenografts. Neoplasia 2001; 3:143-53.

Bhutia, S. K.; Maiti, T. K. Targeting tumors with peptides from natural sources. Trends Biotechnol., 2008, 26(4), 210-217.

Bradley, D. A.; Daignault, S.; Ryan, C. J.; Dipaola, R. S.; Smith, D. C.; Small, E.; Gross, M. E.; Stein, M. N.; Chen, A.; Hussain, M. Cilengitide (EMD 121974, NSC 707544) in asymptomatic metastatic castration resistant prostate cancer patients: a randomized phase II trial by the prostate cancer clinical trials consortium. Invest. New Drugs, 2011, 29(6), 1432-1440.

(Continued)

*Primary Examiner* — Nelson B Moseley, II

(74) *Attorney, Agent, or Firm* — Morgan, Lewis & Bockius LLP

(57) ABSTRACT

Mimetic peptides having anti-angiogenic and anti-tumorigenic properties and methods of their use for treating cancer, ocular diseases, such as age-related macular degeneration, and other-angiogenesis-dependent diseases are disclosed, More particularly, an isolated peptide comprising the amino acid sequence LRRFSTAPFAFIDINDVINF, which exhibits anti-angiogenic activity in endothelial cell proliferation, migration, adhesion, and tube formation assays, anti-migratory activity in human breast cancer cells in vitro, anti-angiogenic and anti-tumorigenic activity in vivo in breast cancer xenograft models, and age-related macular degeneration models is disclosed. The isolate peptide also exhibits anti-lymphangiogenic and directly anti-tumorigenic properties.

29 Claims, 23 Drawing Sheets

Specification includes a Sequence Listing.

(56) References Cited

OTHER PUBLICATIONS

Carmeliet P, Jain RK. Molecular mechanisms and clinical applications of angiogenesis. Nature. May 19, 2011;473 (7347):298-307.
Carmeliet, P. Angiogenesis in life, disease and medicine. Nature, 2005, 438(7070), 932-936.
Carmeliet, P.; Jain, R. K. Angiogenesis in cancer and other diseases. Nature, 2000, 407(6801), 249-257.
Eikesdal, H. P.; Sugimoto, H.; Birrane, G.; Maeshima, Y.; Cooke, V. G.; Kieran, M.; Kalluri, R. Identification of amino acids essential for the antiangiogenic activity of tumstatin and its use in combination antitumor activity. Proc. Natl. Acad. Sci. USA, 2008, 105(39), 15040-15045.
Elkin M and Vlodaysky I. Tail vein assay of cancer metastasis. Curr Protoc Cell Biol Chapter 19: Unit 19 12, 2001.
Folkman J (2002) Role of angiogenesis in tumor growth and metastasis. Semin Oncol; 29: 15-8.
Folkman, J. Tumor angiogenesis: therapeutic implications. N. Engl. J .Med., 1971, 285(21), 1182-1186.
Folkman, J., Angiogenesis. Annu. Rev. Med., 2006, 57, 1-18.
Gautier B, Goncalves V, Diana D, Di Stasi R, Teillet F, Lenoir C, et al. (2010) Biochemical and structural analysis of the binding determinants of a vascular endothelial growth factor receptor peptidic antagonist. J Med Chem; 53: 4428-40.
Gentilucci L, De Marco R, Cerisoli L (2010) Chemical modifications designed to improve peptide stability: incorporation of non-natural amino acids, pseudo-peptide bonds, and cyclization. Curr Pharm Des; 16: 3185-203.
Haviv, F. et al., Thrombospondin-1 mimetic peptide inhibitors of angiogenesis and tumor growth: design, synthesis, and optimization of pharmacokinetics and biological activities. J. Med. Chem., 2005, 48(8), 2838-2846.
Holopainen T, Bry M, Alitalo K, Saaristo A. Perspectives on lymphangiogenesis and angiogenesis in cancer. J Surg Oncol. May 1, 2011; 103(6):484-8.
Hruby VJ, Sharma SD, Toth K, Jaw JY, al-Obeidi F, Sawyer TK, et al. (1993) Design, synthesis, and conformation of superpotent and prolonged acting melanotropins. Ann N Y Acad Sci;680: 51-63.
International Search Report and Written Opinion dated Oct. 23, 2014, from related PCT Patent Application No. PCT/US14/041526.
Karagiannis ED, Popel AS. A systematic methodology for proteome-wide identification of peptides inhibiting the proliferation and migration of endothelial cells. Proc Natl Acad Sci U S A. Sep. 16, 2008; 105(37):13775-80.
Karagiannis, E. D.; Popel, A. S. Identification of novel short peptides derived from the alpha 4, alpha 5, and alpha 6 fibrils of type IV collagen with anti-angiogenic properties. Biochem. Biophys. Res. Commun., 2007, 354(2), 434-439.
Kenny, L. M.; Coombes, R. C.; Oulie, I.; Contractor, K. B.; Miller, M.; Spinks, T. J.; McParland, B.; Cohen, P. S.; Hui, A. M.; Palmieri, C.; Osman, S.; Glaser, M.; Turton, D.; Al-Nahhas, A.; Aboagye, E. 0. Phase I trial of the positron-emitting Arg-Gly-Asp (RGD) peptide radioligand 18F-AH111585 in breast cancer patients. J. Nucl .Med., 2008, 49(6), 879-886.
Koskimaki, J. E.; Karagiannis, E. D.; Rosca, E. V.; Vesuna, F.; Winnard, P. T. Jr.; Raman, V.; Bhujwalla, Z. M.; Popel, A. S., Peptides derived from type IV collagen, CXC chemokines, and thrombospondin-1 domain-containing proteins inhibit neovascularization and suppress tumor growth in MDA-MB-231 breast cancer xenografts. Neoplasia, 2009, 11(12), 1285-1291.
Koskimaki, J. E.; Karagiannis, E. D.; Tang, B. C.; Hammers, H.; Watkins, D. N.; Pili, R.; Popel, A. S. Pentastatin-1, a collagen IV derived 20-mer peptide, suppresses tumor growth in a small cell lung cancer xenograft model. BMC Cancer, 2010, 10, 29.
Lee E, Rosca EV, Pandey NB, Popel AS (2011) Small peptides derived from somatotropin conserved domaincontaining proteins inhibit blood and lymphatic endothelial cell proliferation, migration, adhesion and tube formation. Int J Biochem Cell Biol, 2011, 43(12):1812-1821.
Leung, D. W.; Cachianes, G.; Kuang, W. J.; Goeddel, D. V.; Ferrara, N. Vascular endothelial growth factor is a secreted angiogenic mitogen. Science, 1989, 246(4935), 1306-1309.
Li M, Oliver E, Kitchens KM, Vere J, Alkan SS, Tamiz AP (2008) Structure-activity relationship studies of permeability modulating peptide AT-1002. Bioorg Med Chem Lett;18: 4584-6.
Ma J.S., Unnatural amino acids in drug discovery. Chimica Oggi chemistry today, 2003, 65-68.
Mirochnik, Y.; Aurora, A.; Schulze-Hoepfner, F. T.; Deabes, A.; Shifrin, V.; Beckmann, R.; Polsky, C.; Volpert, 0. V. Short pigment epithelial-derived factor-derived peptide inhibits angiogenesis and tumor growth. Clin. Cancer Res., 2009, 15(5), 1655-1663.
Nabors, L. B.; Fiveash, J. B.; Markert, J. M.; Kekan, M. S.; Gillespie, G. Y.; Huang, Z.; Johnson, M. J.; Meleth, S.; Kuo, H.; Gladson, C. L.; Fathallah-Shaykh, H. M. A phase 1 trial of ABT-510 concurrent with standard chemoradiation for patients with newly diagnosed glioblastoma. Arch. Neurol., 67(3), 313-319.2010.
Ogan MD, Schmiedl U, Moseley ME, Grodd W, Paajanen H, Brasch RC., Albumin labeled with Gd-DTPA. An Intravascular contrast-enhancing agent for magnetic resonance blood pool imaging: preparation and characterization. Invest Radiol. Dec. 1988;23(12):961.
Okamoto N, Tobe T, Hackett SF, Ozaki H, Vinores MA, LaRochelle W, Zack DJ, Campochiaro PA: Transgenic mice with increased expression of vascular endothelial growth factor in the retina: a new model of intraretinal and subretinal neovascularization, Am. J. Pathol. 1997, 151:281-291.
Pernot M, Vanderesse R, Frochot C, Guillemin F, Barberi-Heyob M (2011) Stability of peptides and therapeutic success in cancer. Expert Opin Drug Metab Toxicol;7: 793-802.
Raman V, Artemov D, Pathak AP, Winnard Jr PT, McNutt S, Yudina A, Bogdanov Jr A, Bhujwalla ZM. Characterizing vascular parameters in hypoxic regions: A combined magnetic resonance and optical imaging study of a human prostate cancer model. Cancer Res 2006; 66:9929-36.
Reardon, D.A.; Fink, K. L.; Mikkelsen, T.; Cloughesy, T. F.; O'Neill, A.; Plotkin, S.; Glantz, M.; Ravin, P.; Raizer, J. J.; Rich, K. M.; Schiff, D.; Shapiro, W. R.; Burdette-Radoux, S.; Dropcho, E. J.; Wittemer, S. M.; Nippgen, J.; Picard, M.; Nabors, L. B. Randomized phase II study of cilengitide, an integrin-targeting arginine-glycine-aspartic acid peptide, in recurrent glioblastoma multiforme. J. Clin. Oncol., 2008, 26(34), 5610-5617.
Rivera CG, Rosca EV, Pandey NB, Koskimaki JE, Bader JS, Popel AS (2011) Novel peptide specific (QSAR) analysis applied to collagen IV peptides with antiangiogenic activity. J Med Chem, 54(19):6492-500 (2011).
Rosca EV, Koskimaki JE, Pandey NB, Rivera CG, Tamiz AP, Popel AS (2011) Anti-angiogenic peptides for cancer therapeutics Current Pharmaceutical Biotechnology;12: 1101-16.
Rosca EV, Koskimaki JE, Pandey NB, Wolff AC, Popel AS (2011) Development of a biomimetic peptide derived from collagen IV with anti-angiogenic activity in breast cancer. CancerBiology & Therapy;12:808-17 .
Saladin, P. M.; Zhang, B. D.; Reichert, J. M. Current trends in the clinical development of peptide therapeutics. IDrugs, 2009, 12(12), 779-784.
Senger, D. R.; Galli, S. J.; Dvorak, A. M.; Perruzzi, C. A.; Harvey, V. S.; Dvorak, H. F. Tumor cells secrete a vascular permeability factor that promotes accumulation of ascites fluid. Science, 1983, 219(4587), 983-985.
Tobe T, Okamoto N, Vinores MA, Derevjanik NL, Vinores SA, Zack DJ, Campochiaro PA: Evolution of neovascularization in mice with overexpression of vascular endothelial growth factor in photoreceptors, Invest. Ophthalmol. Vis. Sci. 1998, 39:180-188.

\* cited by examiner

CM CONTROL

SP2043 25 μM

CTRL (EGM-2MV)

MEC TUBE FORMATION

SP2043 25 μM

CONTROL

SP2043

BIOMIMETIC PEPTIDE AND BIODEGRADABLE DELIVERY PLATFORM FOR THE TREATMENT OF ANGIOGENESIS- AND LYMPHANGIOGENESIS-DEPENDENT DISEASES

This application is a continuation of U.S. patent application Ser. No. 14/896,521, filed Dec. 7, 2015 and issued as U.S. Pat. No. 9,802,984 on Oct. 31, 2017. U.S. Ser. No. 14/896,521 claims the benefit of U.S. Provisional Application No. 61/832,290, filed Jun. 7, 2013. The contents of the aforementioned patent applications are incorporated herein by reference in their entireties.

FEDERALLY SPONSORED RESEARCH OR DEVELOPMENT

This invention was made with government support under R21 CA131931 and R01 CA138264 awarded by the National Institutes of Health. The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "ASX-006C1_Sequence_Listing_ST25.txt". The sequence listing is 2,381 bytes in size, and was electronically filed via EFS-Web on Sep. 22, 2017. The sequence listing is hereby incorporated by reference in its entirety.

BACKGROUND

Cancer is a major public health problem in the United States and other parts of the world. Currently, 1 in 4 deaths in the United States is due to cancer. Angiogenesis plays a critical role in tumor growth and metastasis in most types of cancer. In particular, its importance has been demonstrated in breast cancer, the most commonly diagnosed female malignancy in the United States. Anti-angiogenic therapeutics, either as a monotherapy or in combination with other therapeutics, are promising and are being intensely investigated in both preclinical and clinical studies. Anti-VEGF therapeutics showed early promise in clinical trials; however, although an anti-VEGF antibody bevacizumab (Genentech/Roche) was approved by the Food and Drug Administration (FDA) for breast cancer in 2008 in combination with chemotherapy, in November 2011, the FDA revoked the breast cancer indication because it has not demonstrated an overall survival benefit.

The development of anti-angiogenic therapies to treat breast and other cancers, as well as, ocular proliferative diseases, such as age-related macular degeneration, is ongoing. Lymphangiogenesis also plays an important role in cancer metastasis (Holopainen et al., 2011). To date, no peptide drugs have been approved for the treatment of cancer or other angiogenesis- and lymphangiogenesis-dependent diseases.

Peptides have been employed as therapeutics for multiple diseases and recently have been investigated in clinical applications to target tumors either for imaging or therapy (Folkman, 2010; Senger et al., 1983; Leung et al., 1989; Carmeliet, 2005; Carmeliet and Jain, 2000; Carmeliet and Jain, 2011; Rosca et al., 2011). Mimetic peptides are peptides that biologically mimic active determinants on biomolecules. In general, peptides are attractive tools as therapeutics due to their specific target binding, ability to penetrate cells and ease of modification giving flexibility for different applications (Carmeliet and Jain, 2000; Folkman, 2006). In addition, they are less toxic because they bind to their targets with high specificity and they are inexpensive to produce.

Some of the properties that make peptides attractive candidates, however, also contribute to their disadvantages. Although peptides can interact specifically with cellular receptors, sometimes these interactions may be of low affinity. In addition, the use of peptides as therapeutic agents is currently limited due to their short half-life and reduced bioavailability. Attempts to modify a peptide to increase its bioavailability include substitution with non-natural amino acids, pegylation of the peptide, and delivery of the peptide in a nano- or micro-particle.

SUMMARY

The presently disclosed subject matter provides peptide compositions, methods, and kits for treating a disease, disorder, or dysfunction that is related to angiogenesis, lymphangiogenesis, vascular permeability and/or tumorigenesis. The presently disclosed peptide compositions and methods, in some aspects, inhibit angiogenesis, lymphangiogenesis, vascular permeability and/or tumorigenesis, which play a critical role in multiple diseases or disorders. Accordingly, in some aspects, the compositions and methods of the presently disclosed subject matter allow the prevention or reduction of blood vessel, lymphatic vessel, or tumor formation involving a cell, tissue or organ.

In some aspects, the presently disclosed subject matter provides an isolated peptide comprising an amino acid sequence at least 85% identical to LRRFSTAPFAFIDINDVINF (SEQ ID NO:1), wherein the peptide exhibits anti-angiogenic, anti-vascular permeability, anti-tumorigenesis and/or anti-lymphangiogenic properties.

In other aspects, the presently disclosed subject matter provides a composition comprising a pharmaceutically acceptable carrier and an effective amount of an isolated peptide comprising an amino acid sequence at least 85% identical to LRRFSTAPFAFIDINDVINF (SEQ ID NO:1), wherein the peptide exhibits anti-angiogenic, anti-vascular permeability, anti-tumorigenesis and/or anti-lymphangiogenic properties.

In further aspects, the presently disclosed subject matter provides a kit comprising an isolated peptide comprising an amino acid sequence at least 85% identical to LRRFSTAPFAFIDINDVINF (SEQ ID NO:1), wherein the peptide exhibits anti-angiogenic, anti-vascular permeability, anti-tumorigenesis and/or anti-lymphangiogenic properties.

In still further aspects, the presently disclosed subject matter provides a nanoparticle or microparticle comprising an isolated peptide comprising an amino acid sequence at least 85% identical to LRRFSTAPFAFIDINDVINF (SEQ ID NO:1), wherein the peptide exhibits anti-angiogenic, anti-vascular permeability, anti-tumorigenesis and/or anti-lymphangiogenic properties.

In some aspects, the presently disclosed subject matter provides a method for inhibiting angiogenesis, lymphangiogenesis, vascular permeability and/or tumorigenesis involving a cell, the method comprising: contacting the cell with an isolated peptide comprising an amino acid sequence at least 85% identical to LRRFSTAPFAFIDINDVINF (SEQ ID NO:1), in an amount sufficient to inhibit angiogenesis, lymphangiogenesis, vascular permeability and/or tumorigenesis involving the cell.

In some other aspects, the presently disclosed subject matter provides a method for treating a subject suffering from a disease related to angiogenesis, lymphangiogenesis, vascular permeability, and/or tumorigenesis or to prevent or delay a subject from developing a disease related to angiogenesis, lymphangiogenesis, vascular permeability, and/or tumorigenesis, the method comprising: administering to the subject an isolated peptide comprising an amino acid sequence at least 85% identical to LRRFSTAPFAFIDINDVINF (SEQ ID NO:1), in an amount sufficient to treat, delay, or prevent the disease in the subject.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
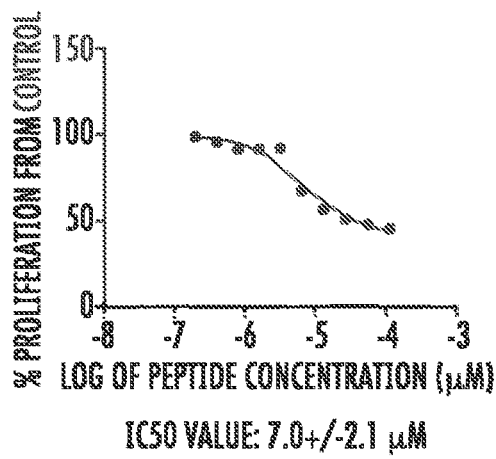
Figure 1B:
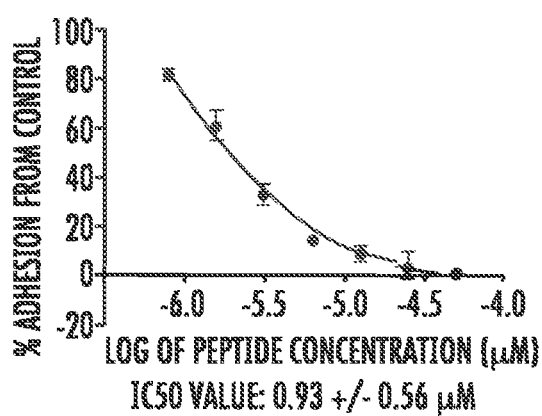
Figure 1C:
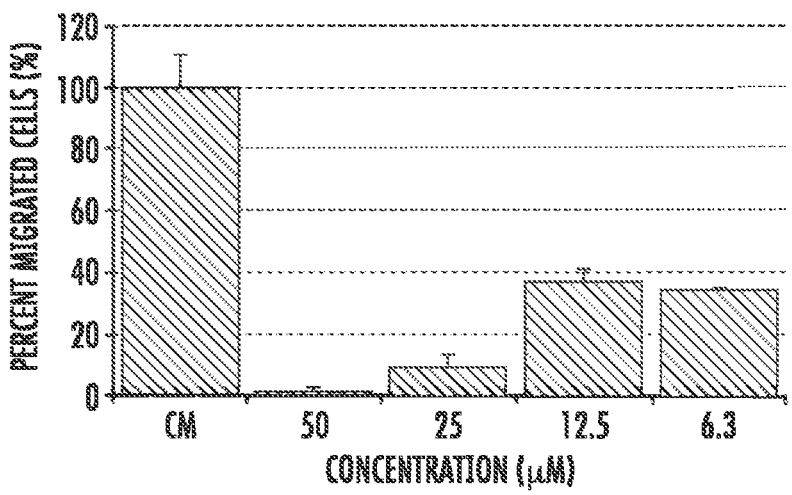
Figure 2A:
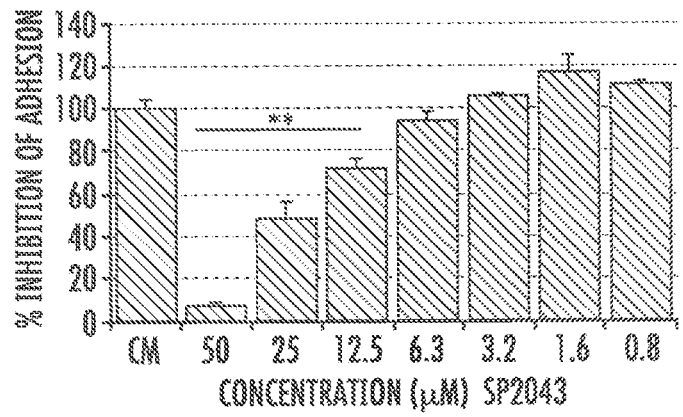
Figure 2B:
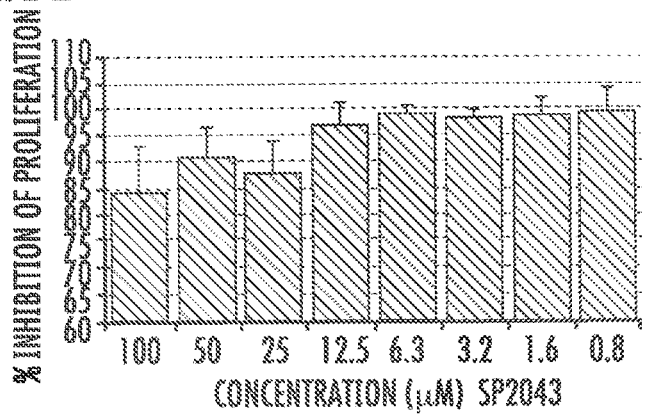
Figure 2C:
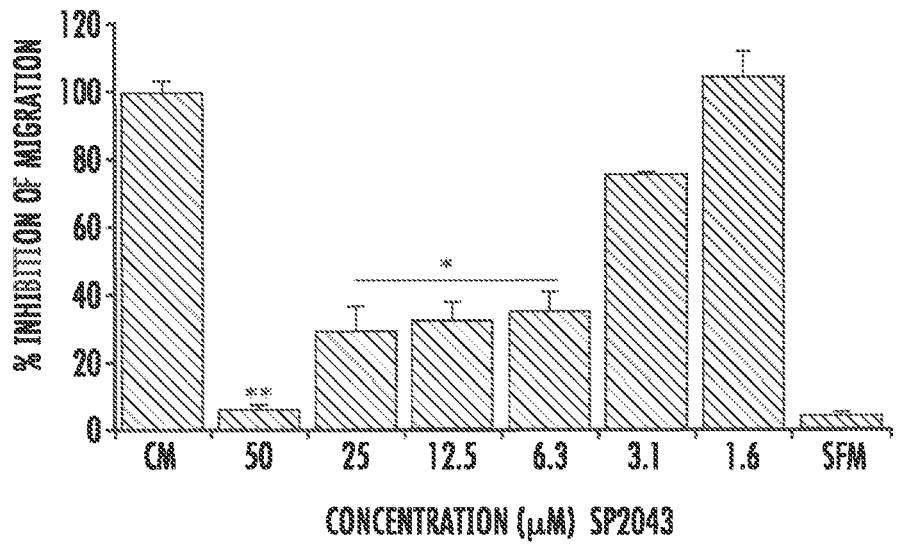
Figure 3A:
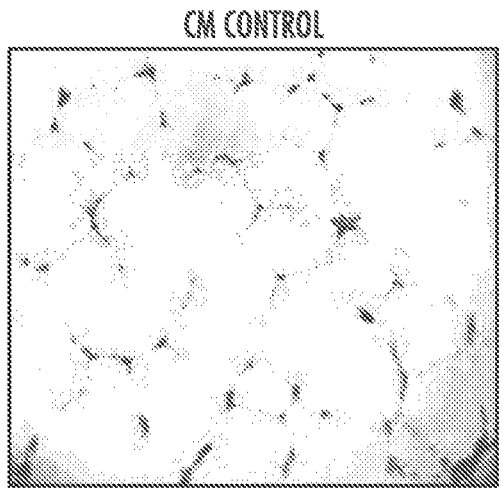
Figure 3B:
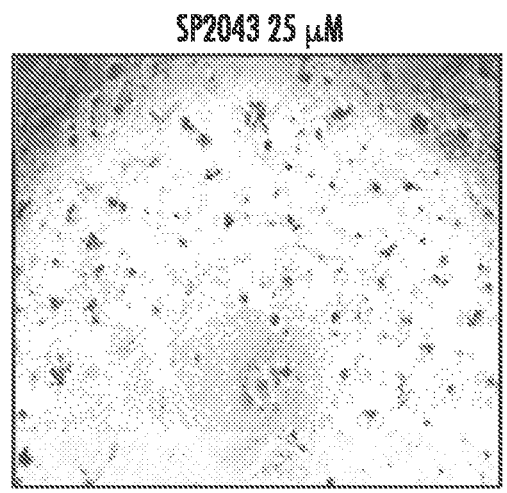
Figure 3C:
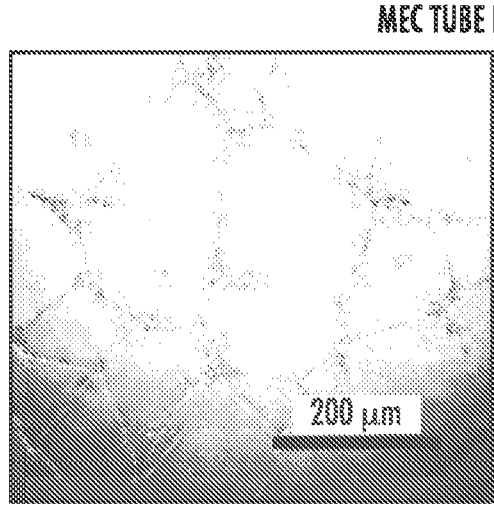
Figure 3D:
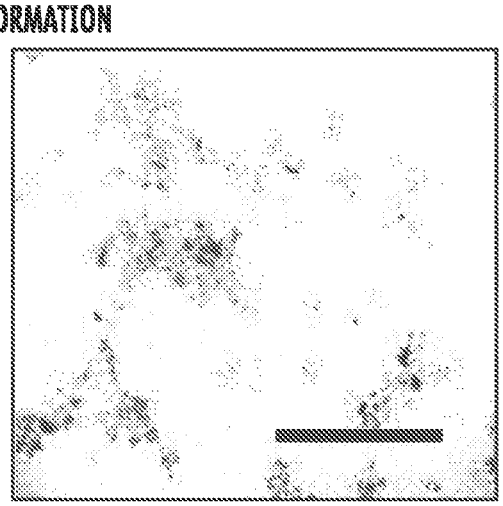
Figure 4:
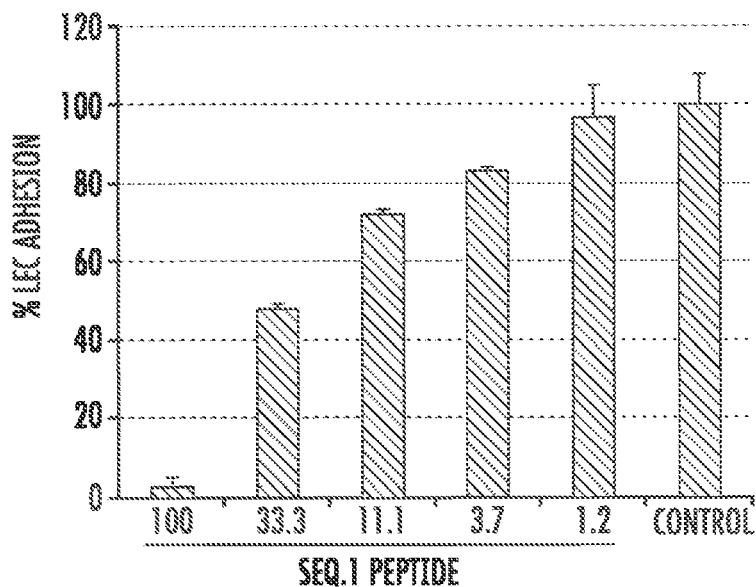
Figure 5:
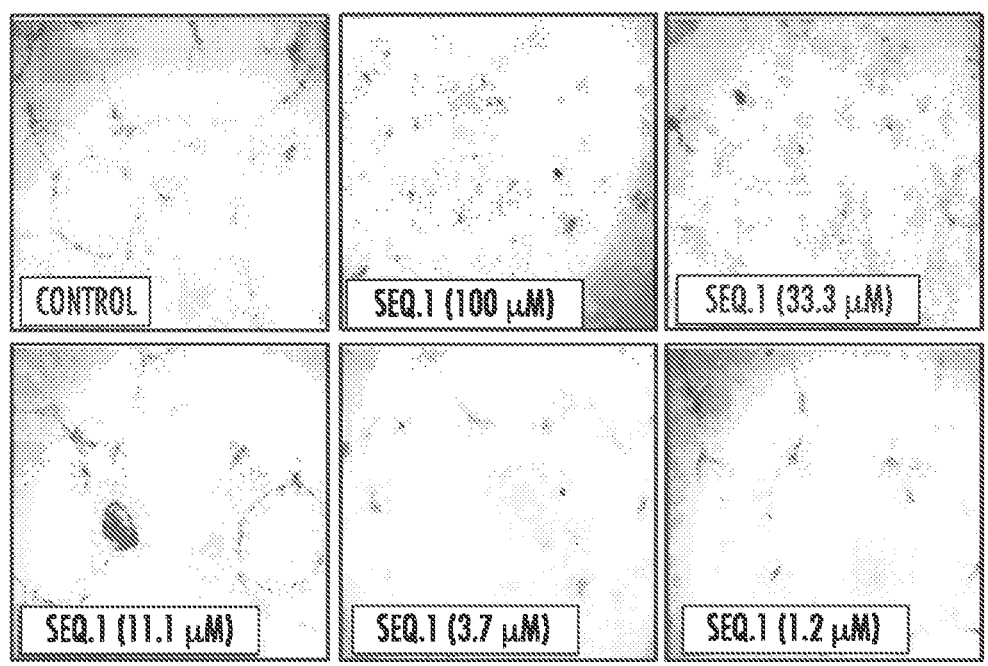
Figure 6A:
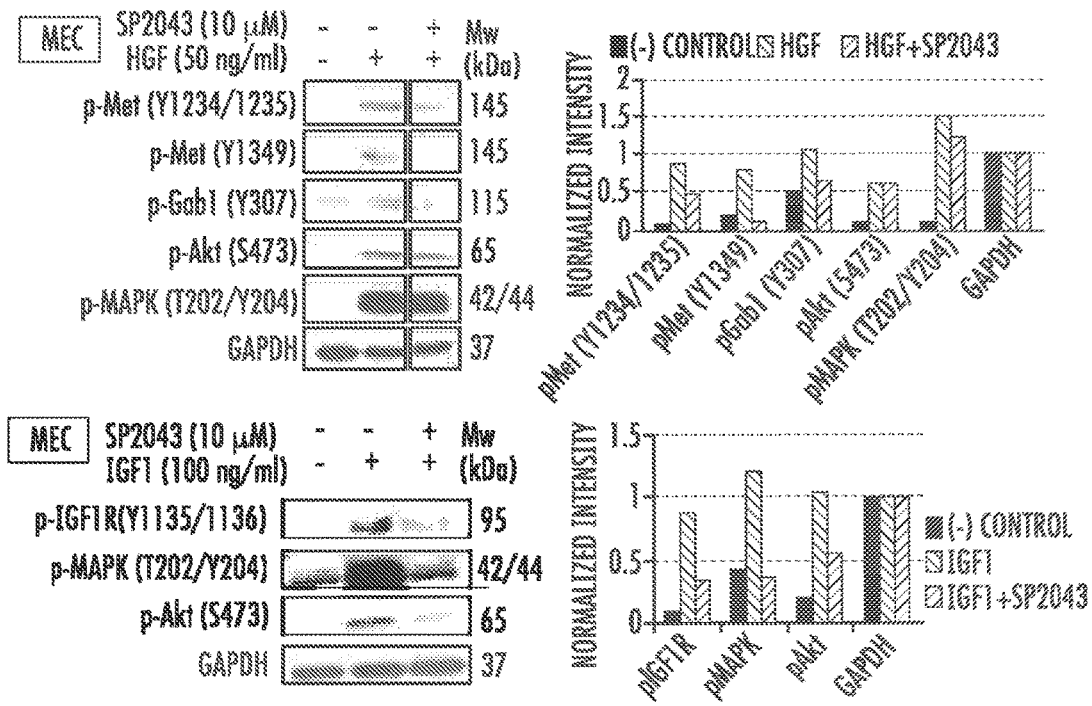
Figure 6B:
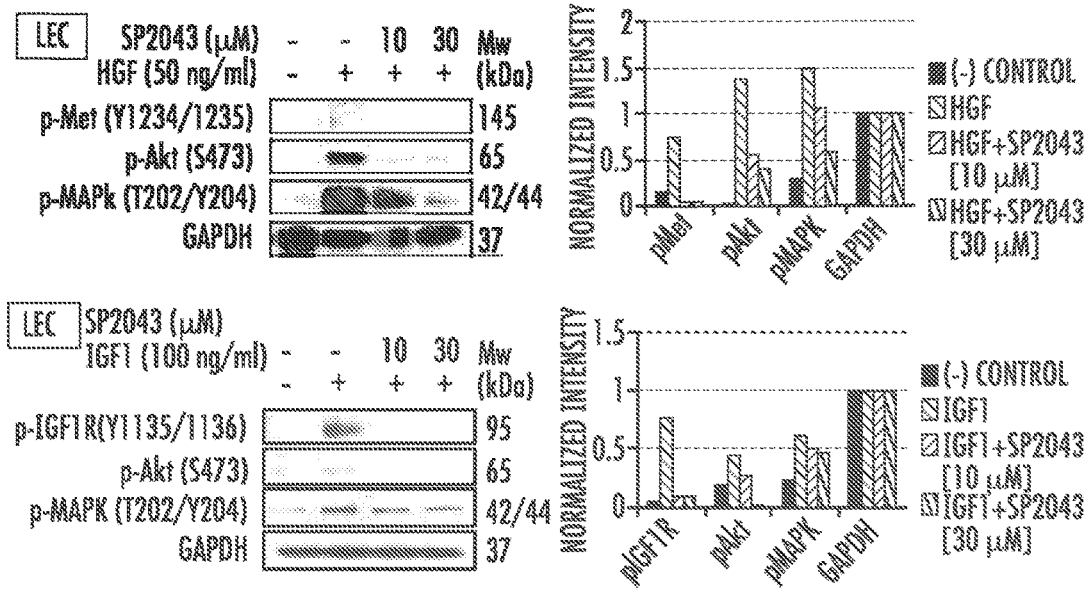
Figure 7:
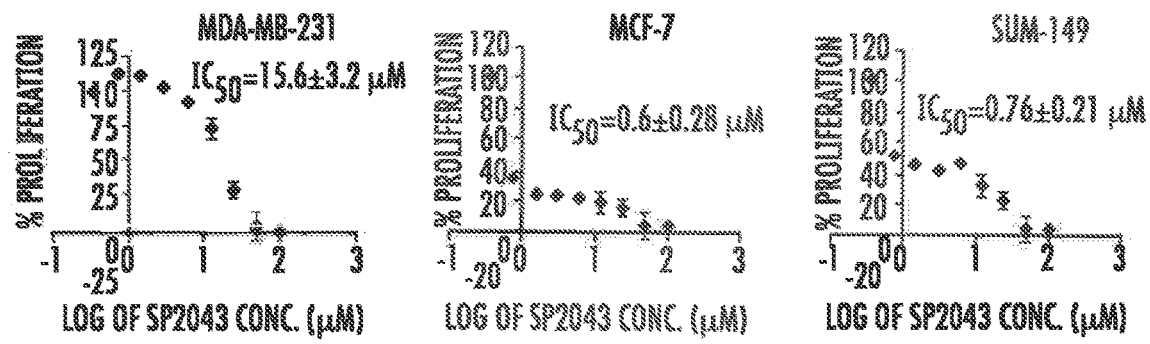
Figure 8:
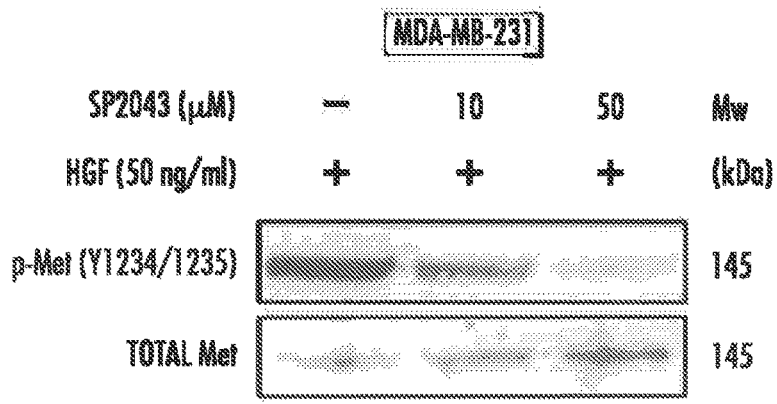
Figure 9:
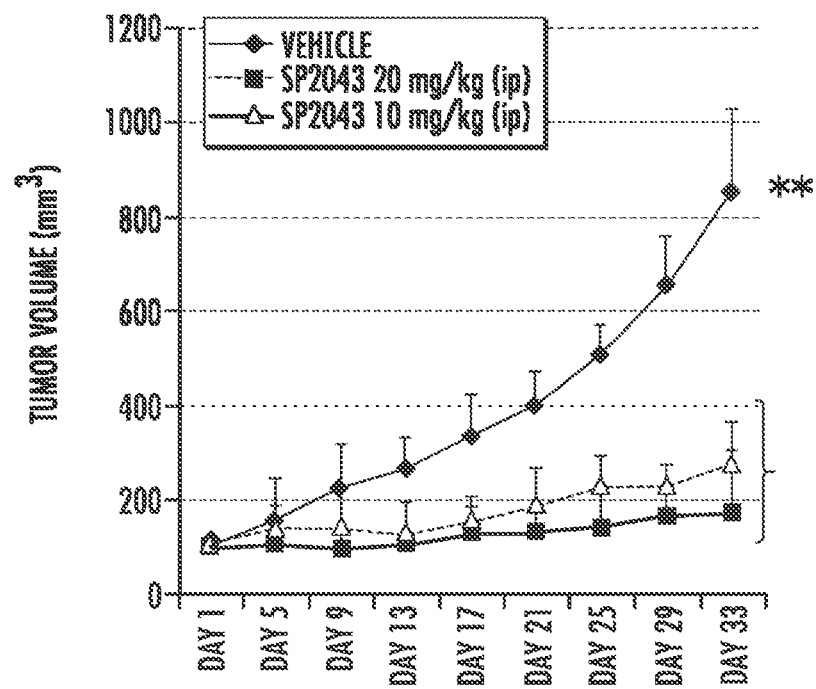
Figure 10A:
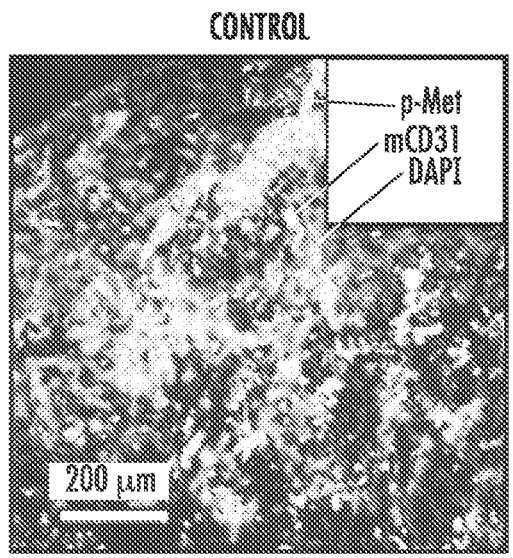
Figure 10B:
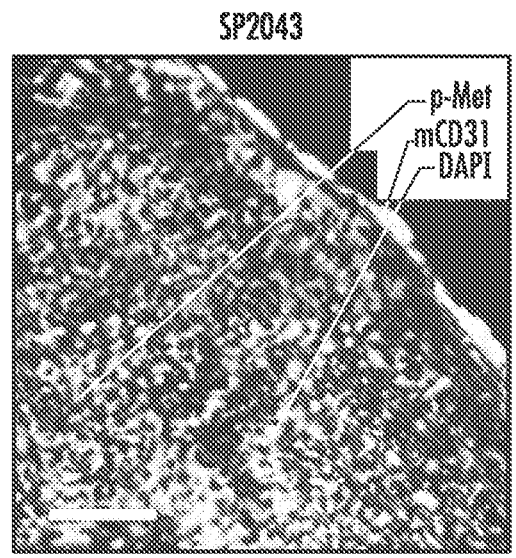
Figures 11A, 11B, 11C, 11D:
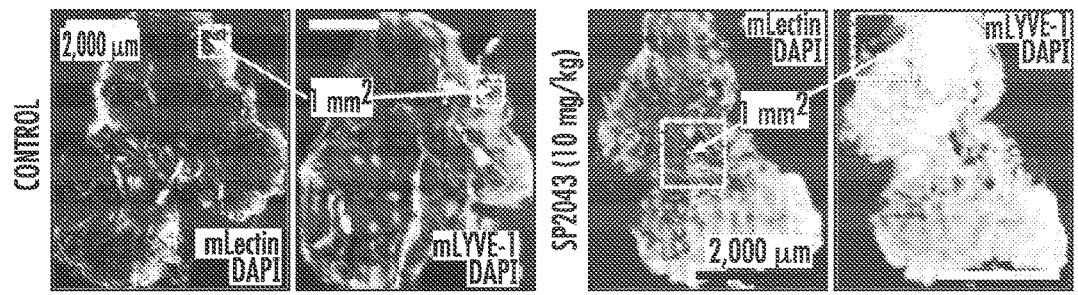
Figure 11E:
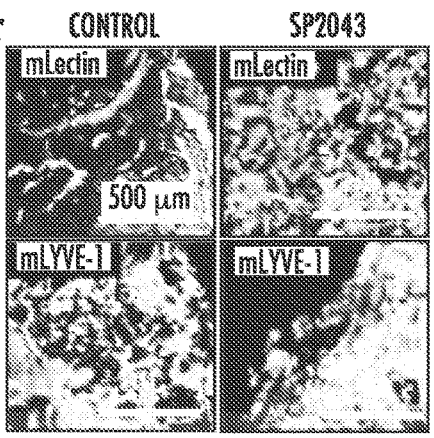
Figure 11F:
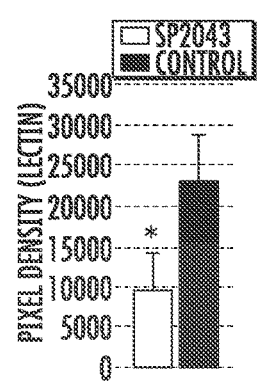
Figure 11G:
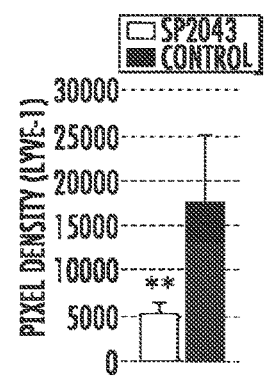
Figure 12A:
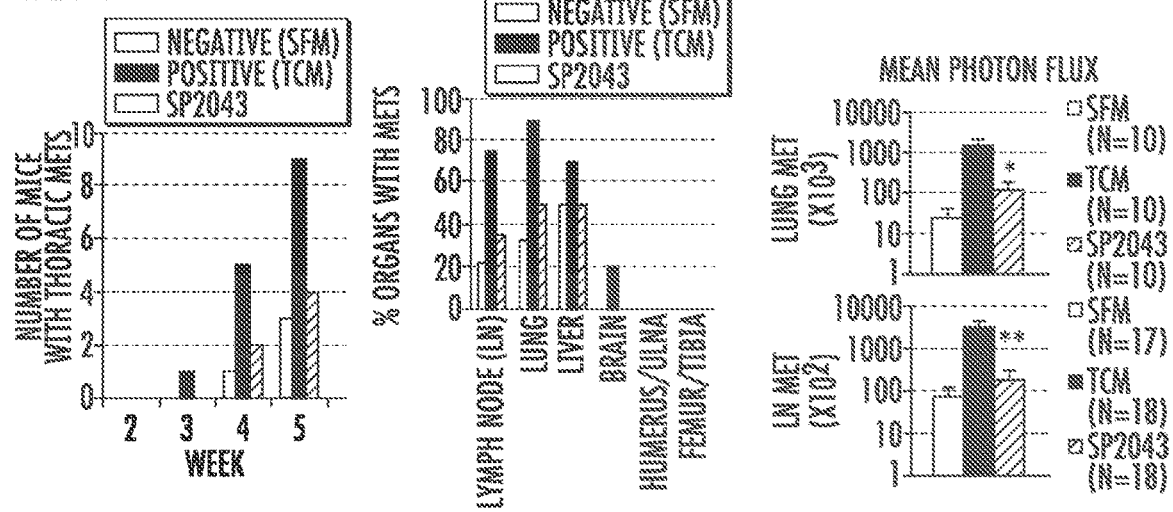
Figure 12B:
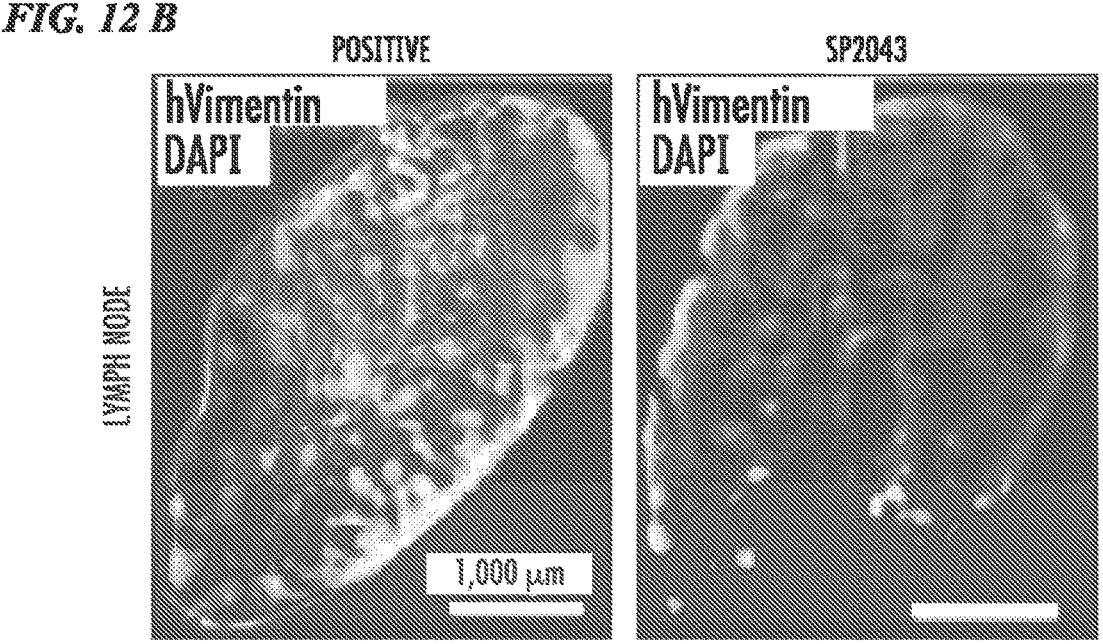
Figure 14:
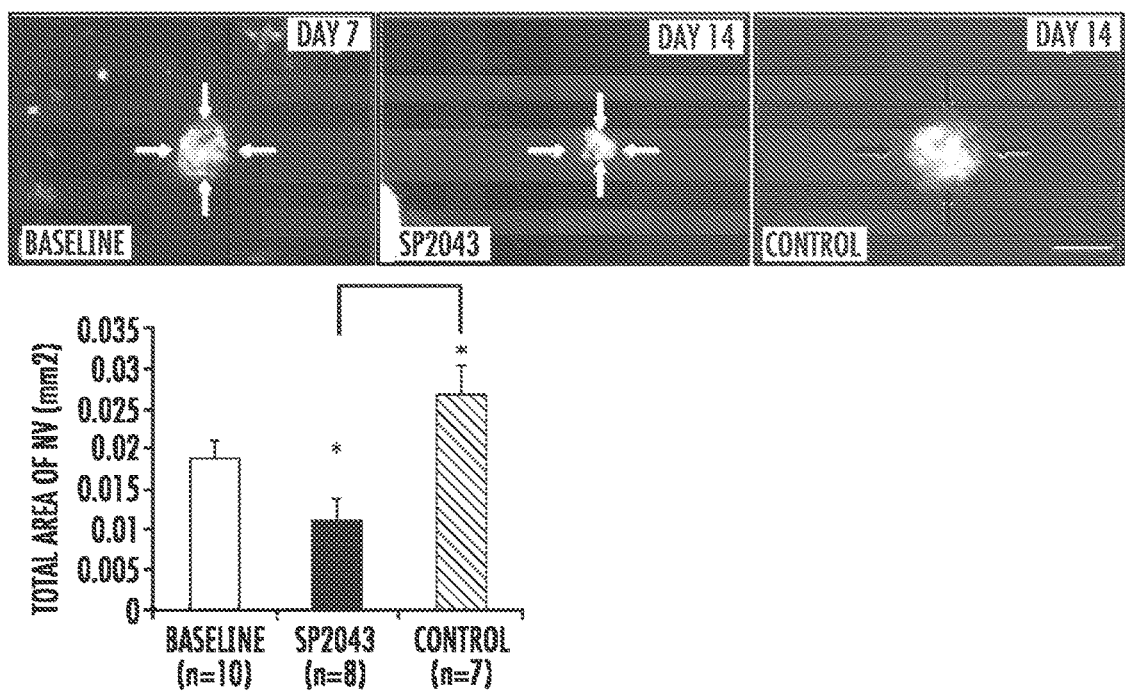
Figure 15:
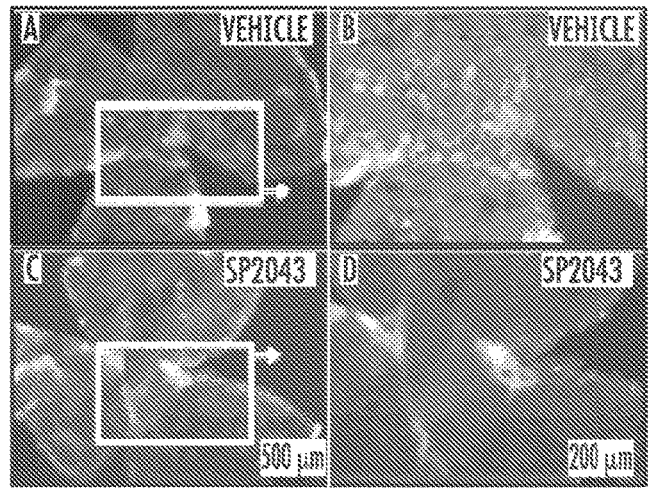
Figure 15:
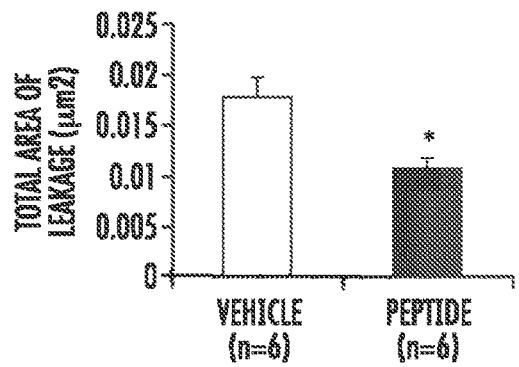
Figure 16:
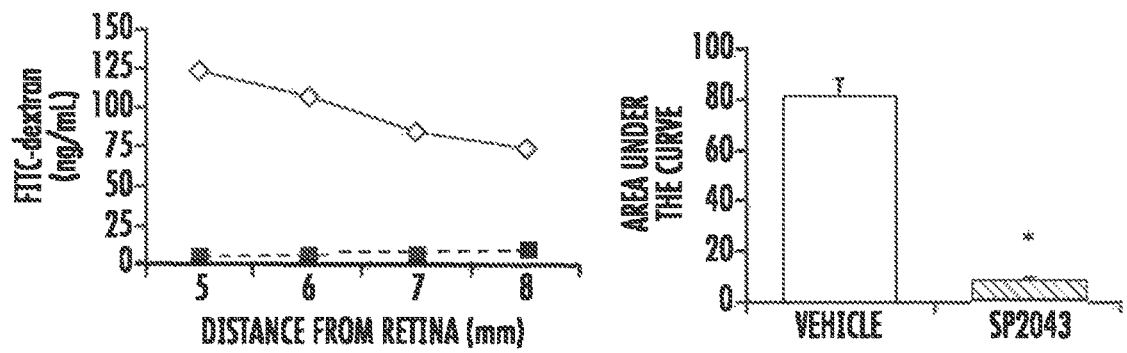
Figure 17:
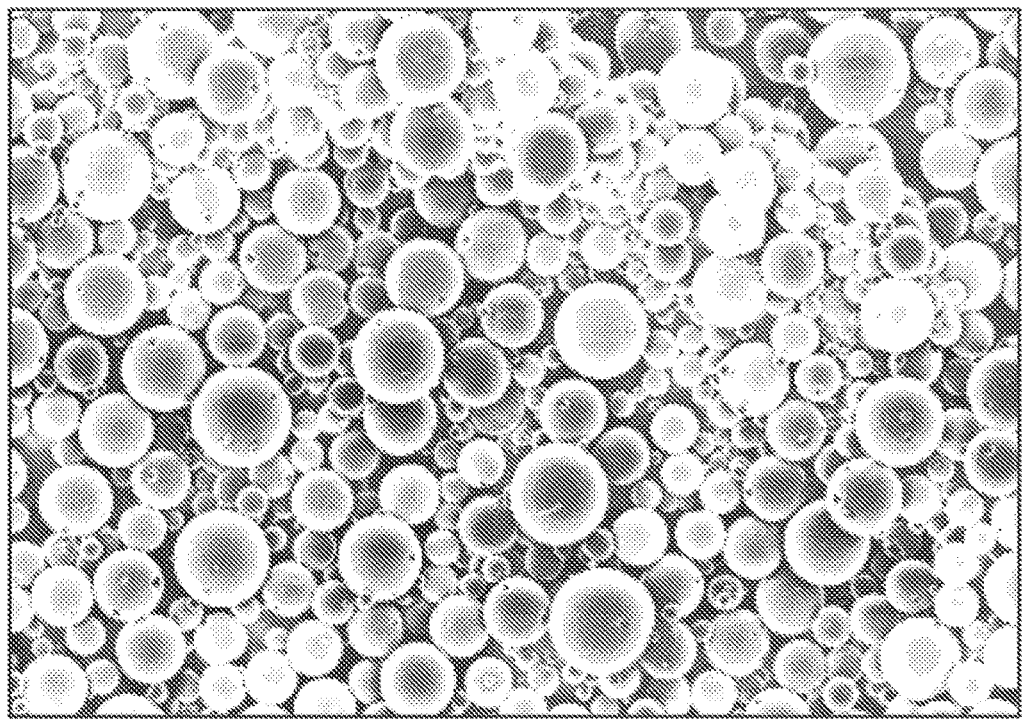
Figure 18A:
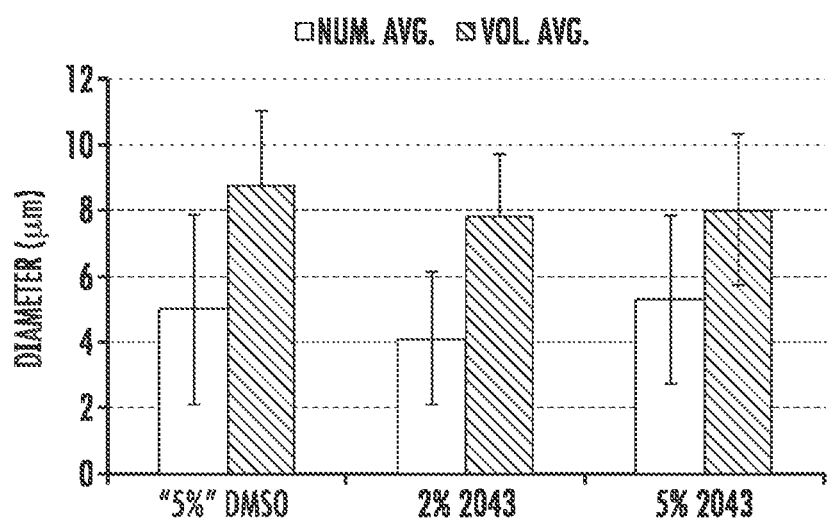
Figure 18B:
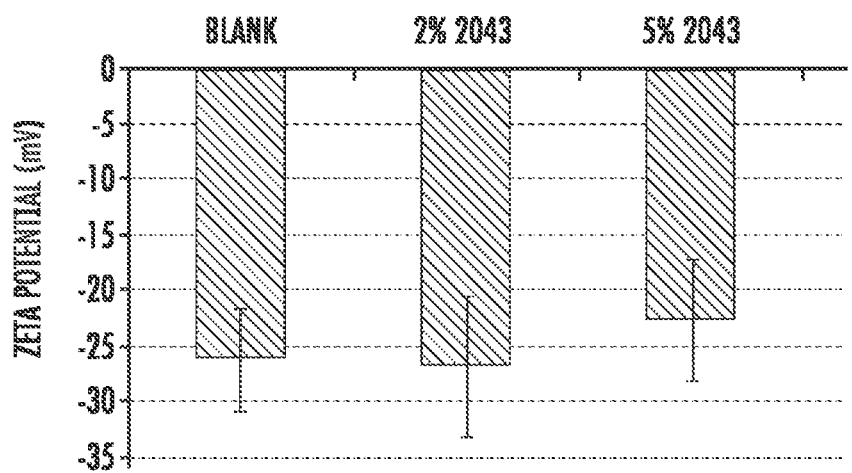
Figure 19A:
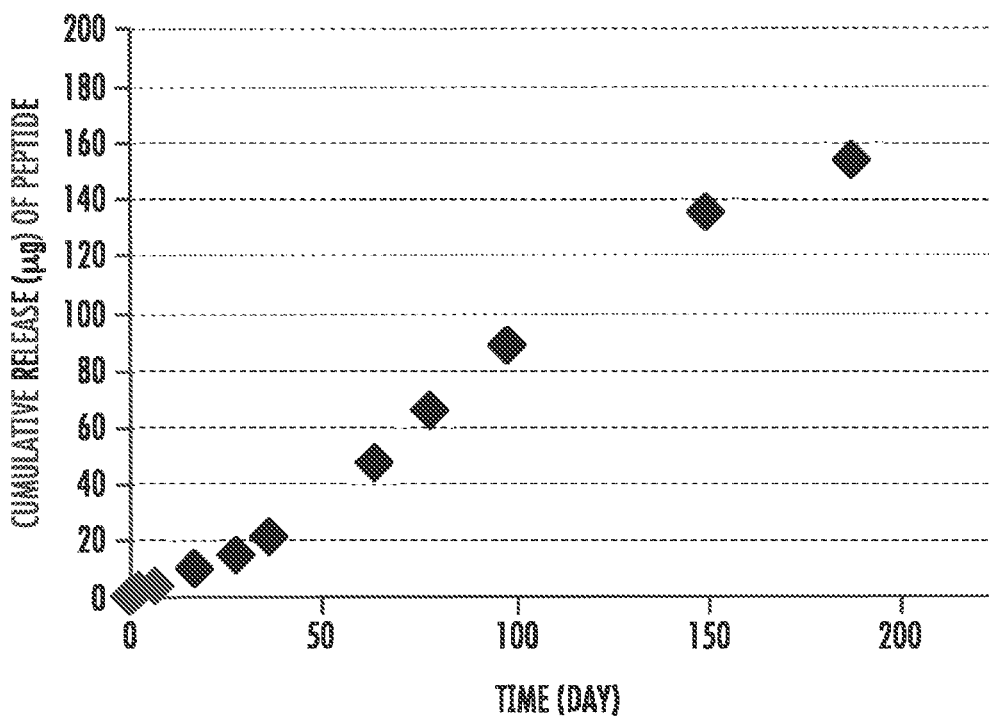
Figure 19B:
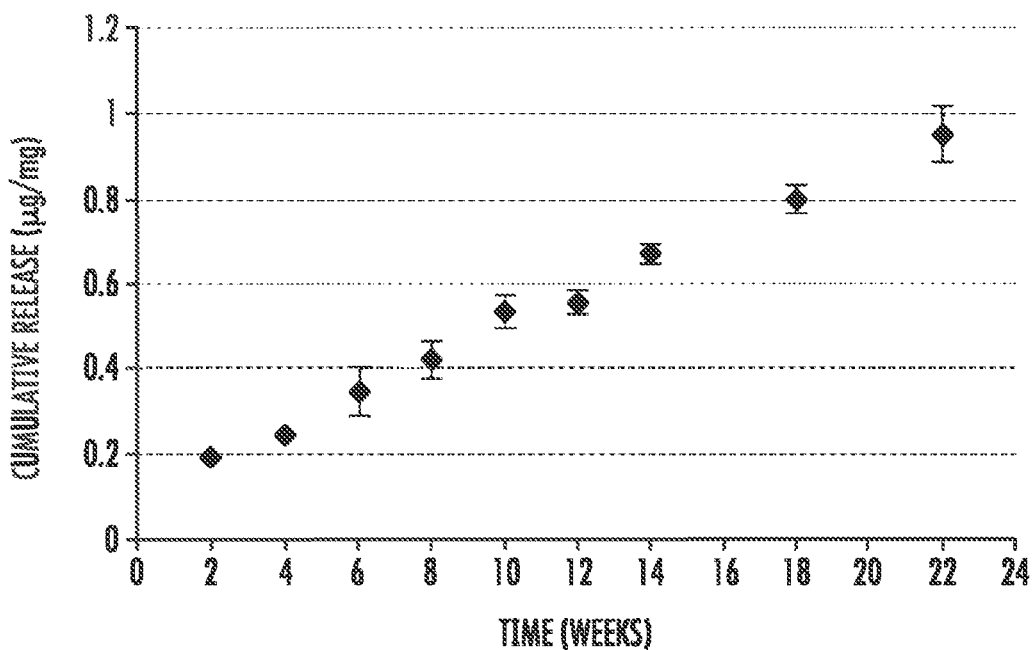
Figure 20:
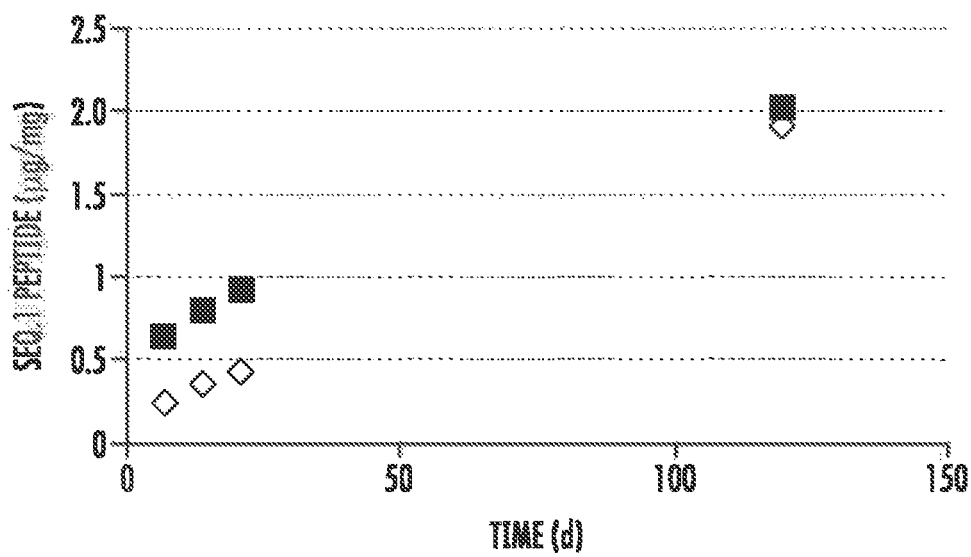
Figure 21:
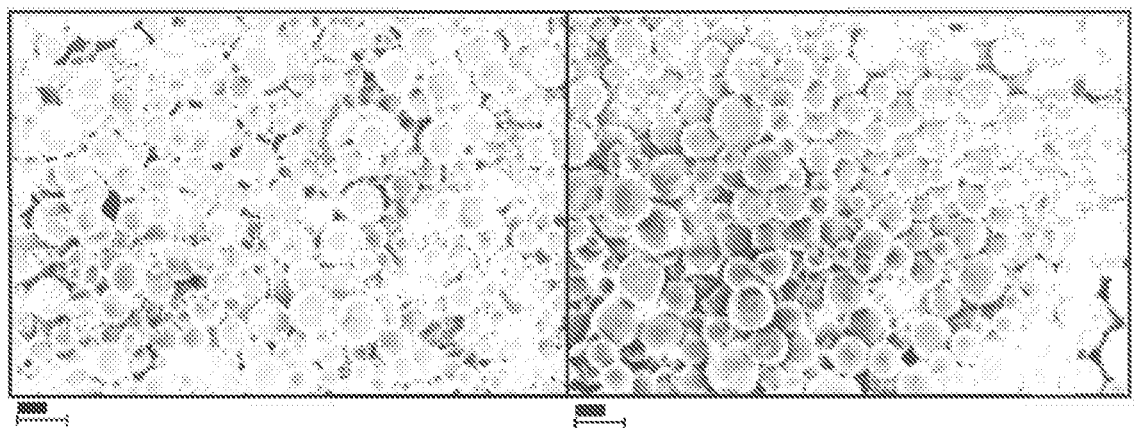
Figure 22:
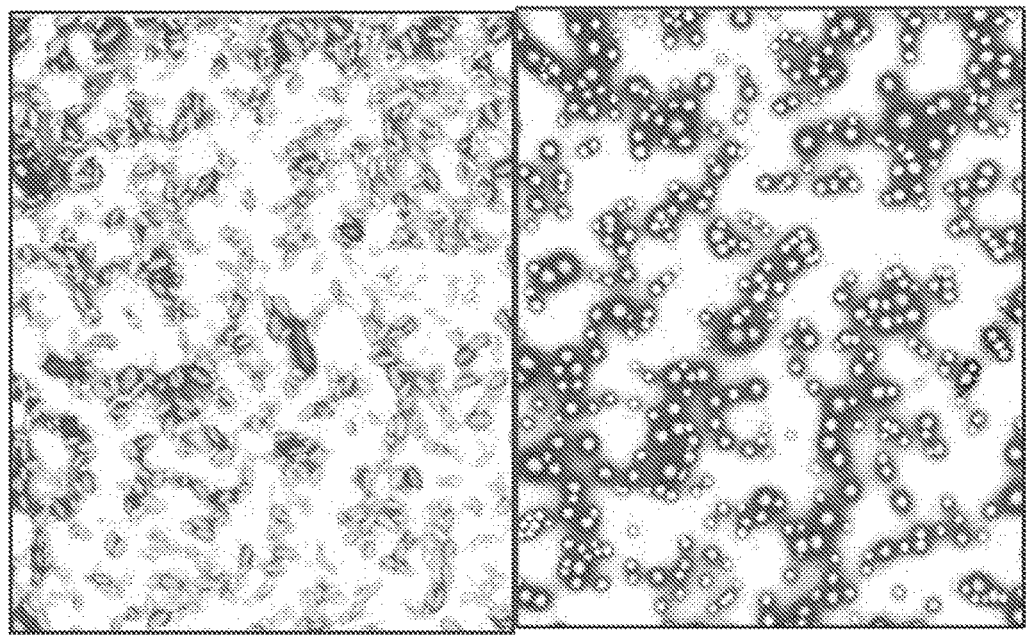
Figure 23:
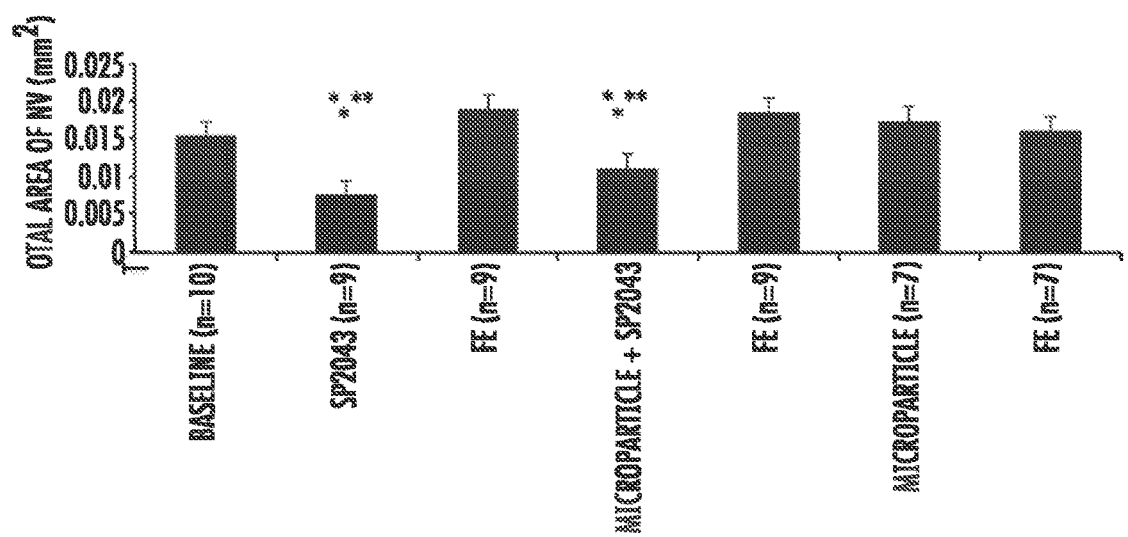
Figure 24:
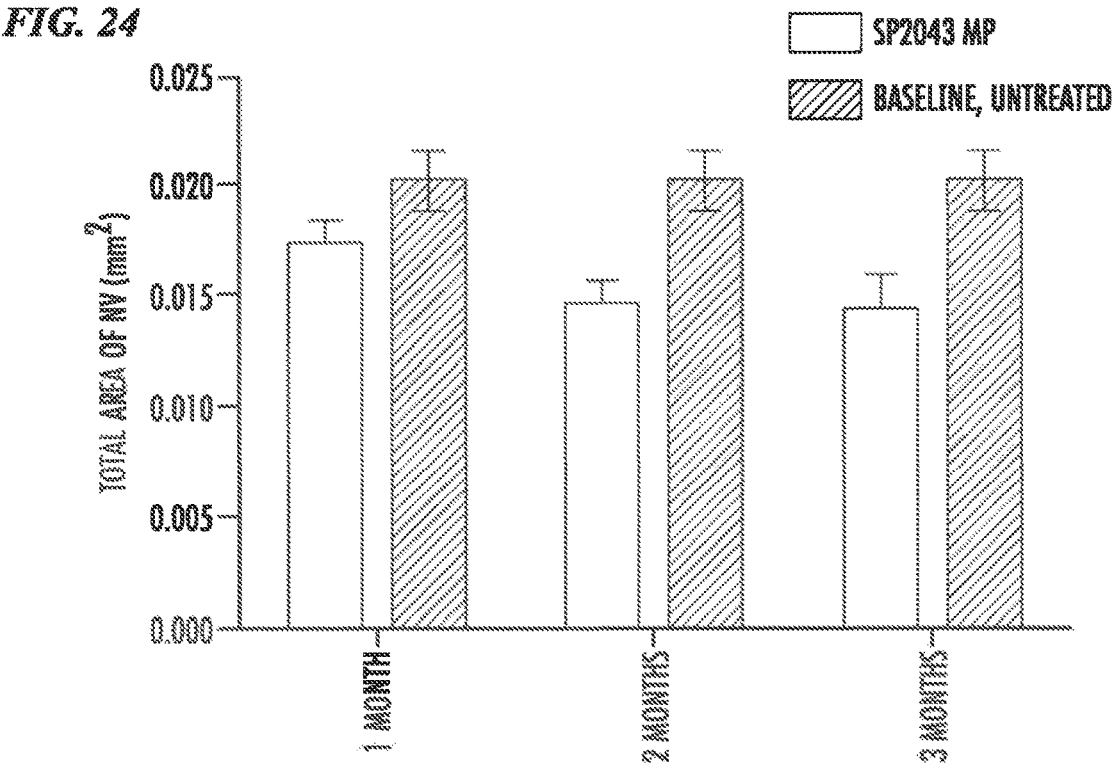
Figure 25:
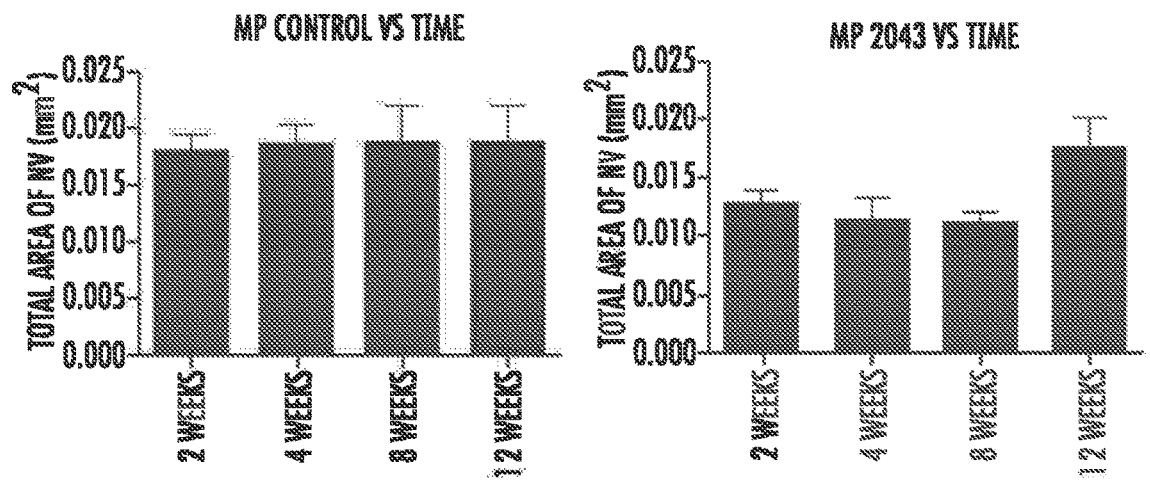
Figure 26:
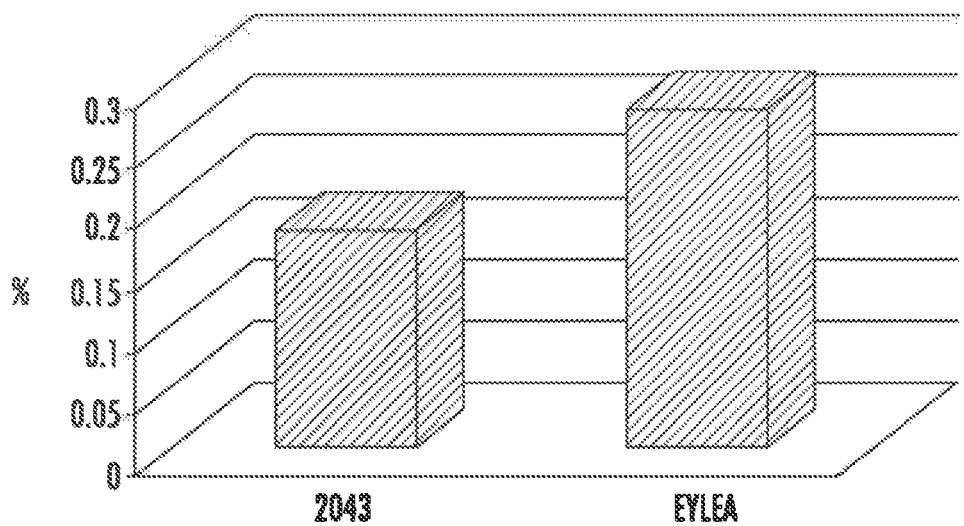
Figure 27:
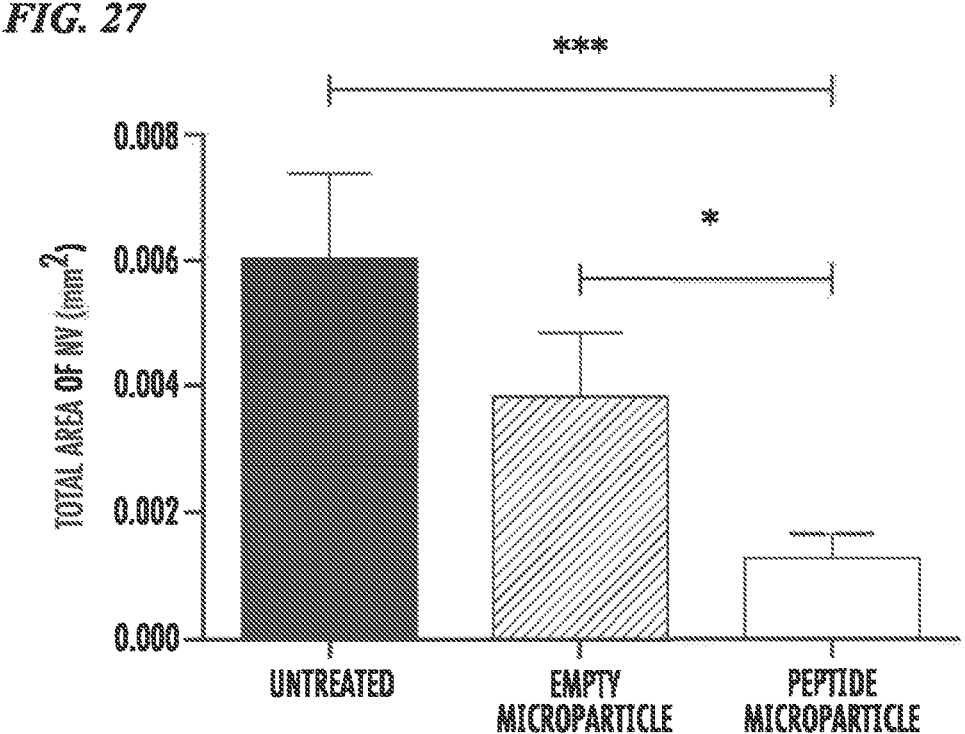
Figure 28:
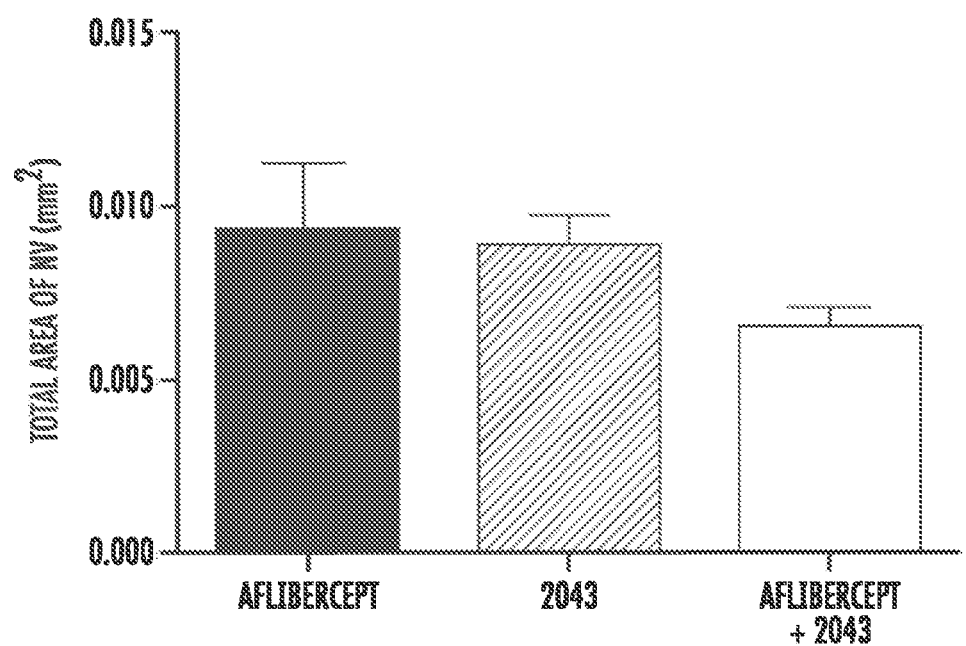
Figure 29:
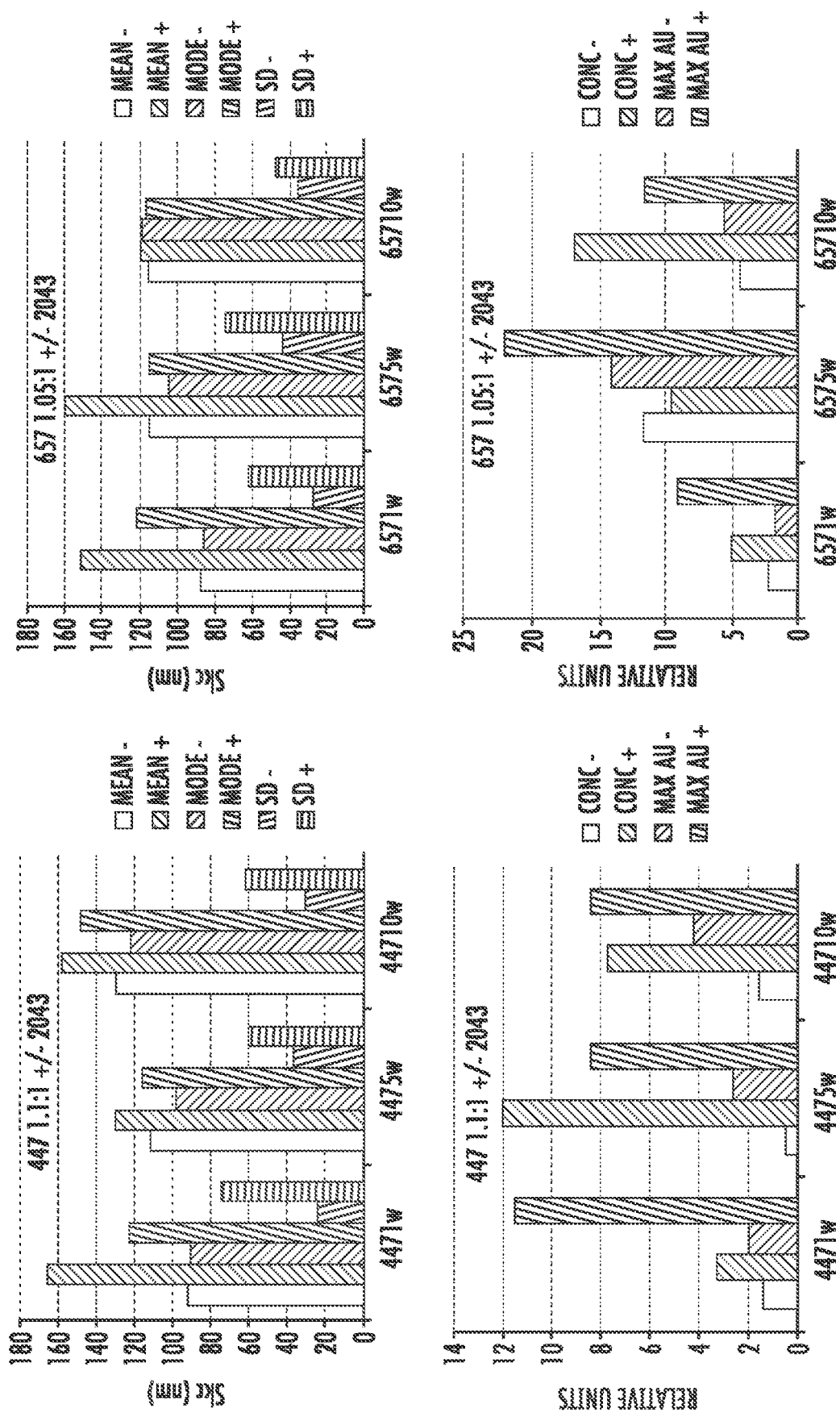
Figure 30:
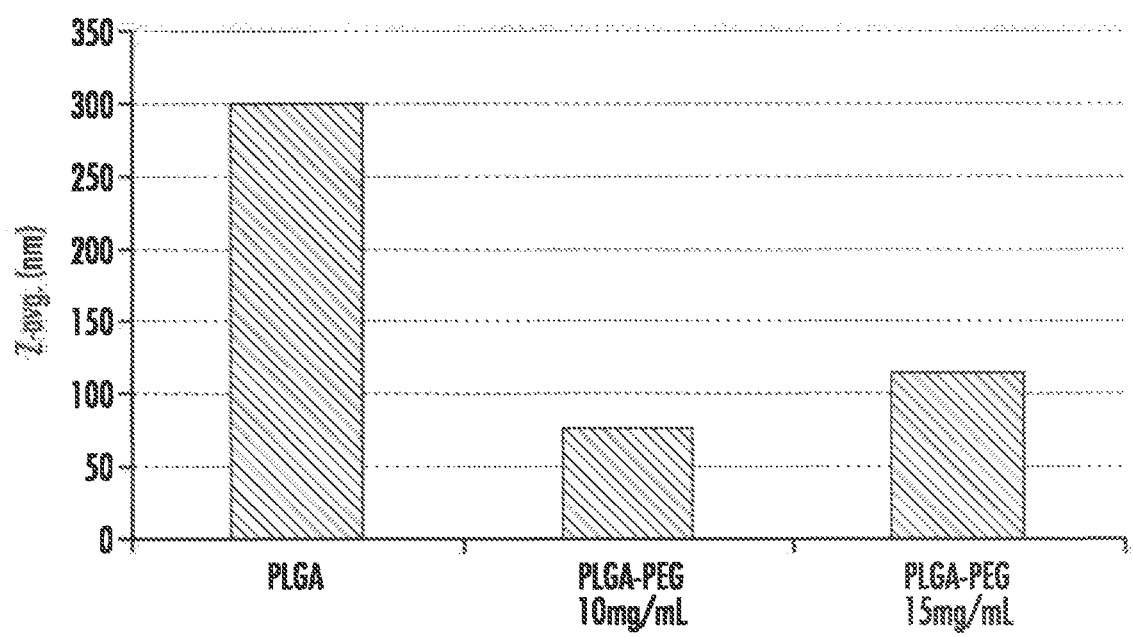
Figure 31A:
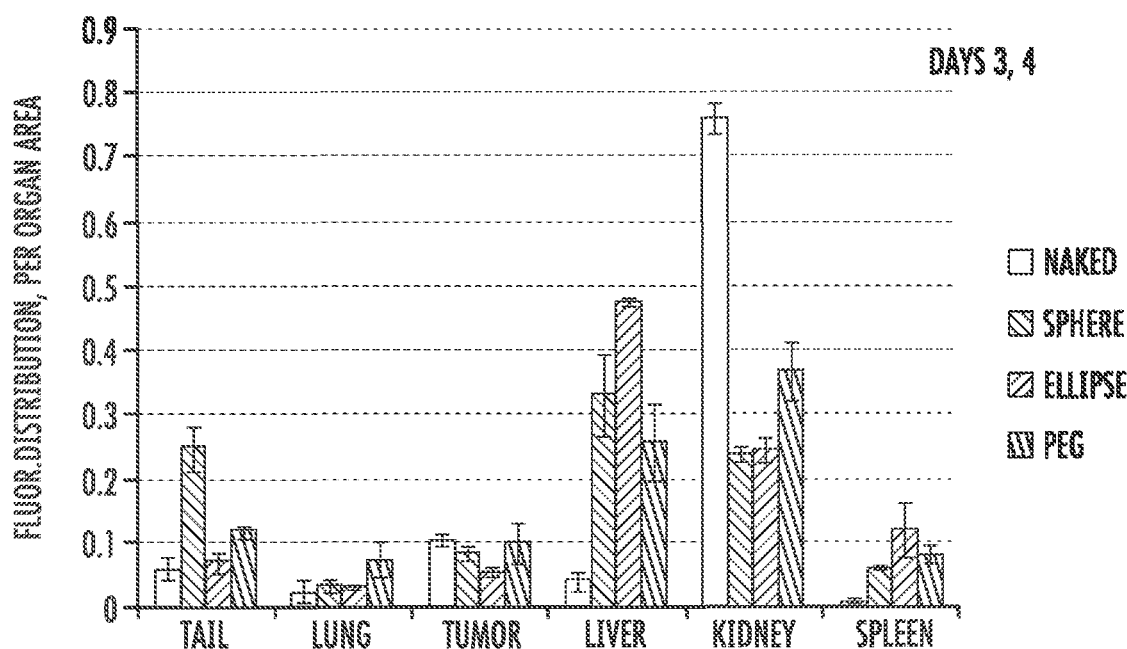
Figure 31B:
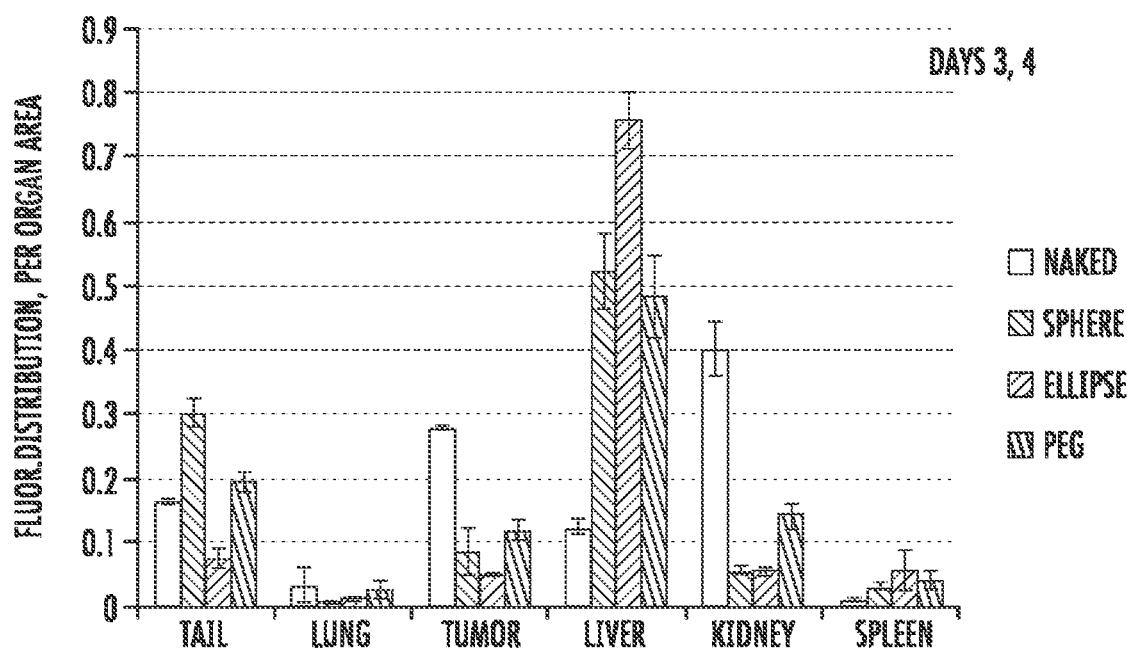
Figure 32A:
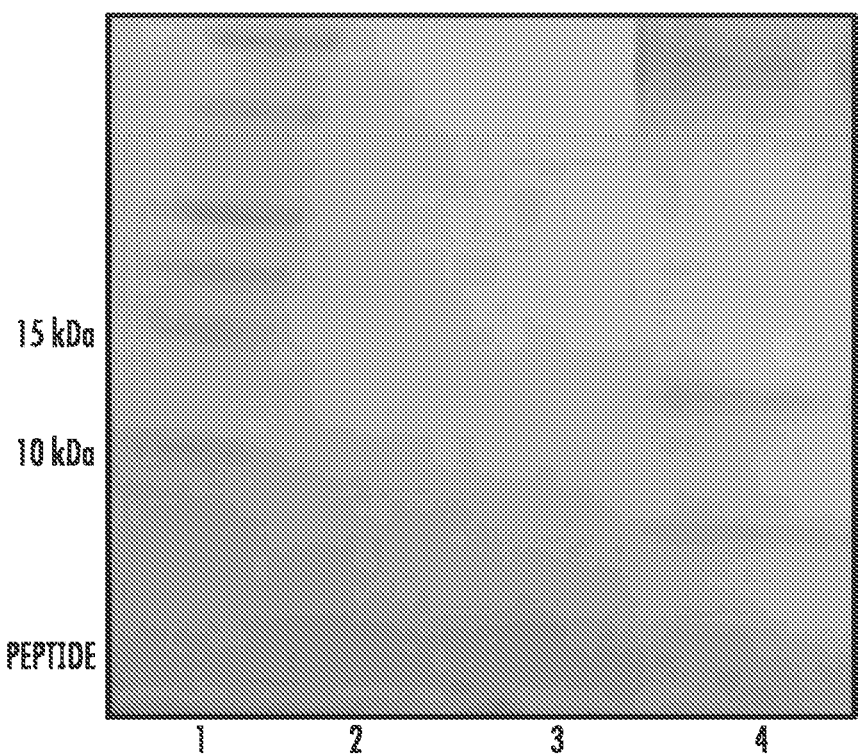
Figure 32B:
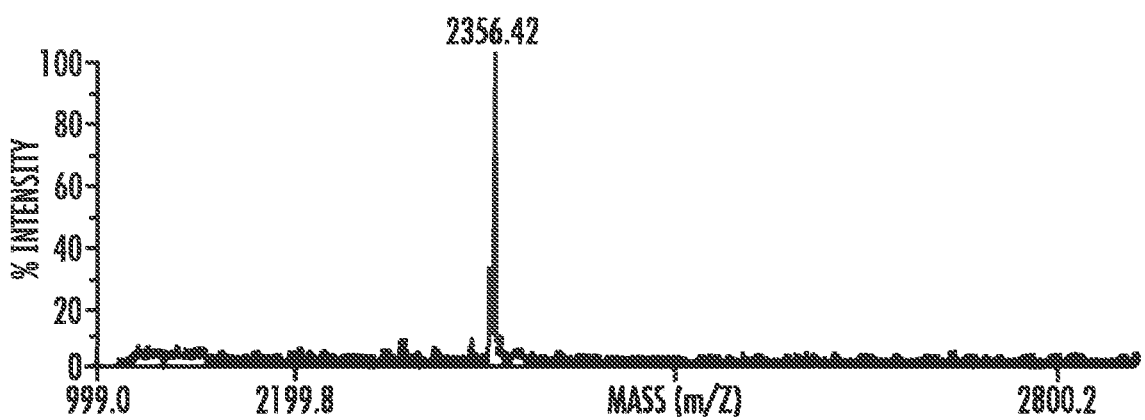

Having thus described the presently disclosed subject matter in general terms, reference will now be made to the accompanying Figures, which are not necessarily drawn to scale, and wherein:

FIGS. 1A-1C show proliferation (Panel A), adhesion (Panel B), and migration (Panel C) using the SP2043 peptide (SEQ ID NO:1) with human umbilical vein endothelial cells (HUVEC);

FIGS. 2A-2C show adhesion (Panel A), proliferation (Panel B), and migration (Panel C) using the SP2043 peptide (SEQ ID NO:1) with human retinal endothelial cells (HREC);

FIGS. 3A-3D show a HUVEC tube formation assay using a CM control (Panel A) and the SP2043 peptide (SEQ ID NO:1) (25 μM SP2043 peptide; Panel B); and a microvascular endothelial cell (MEC) tube formation assay using a control (Ctrl; Panel C) and the SP2043 peptide (SEQ ID NO:1) (25 μM SP2043 peptide; Panel D);

FIG. 4 shows the effect of the SP2043 peptide (SEQ ID NO:1), also referred to herein and in the Figures as SEQ.1, on lymphatic endothelial cell (LEC) adhesion;

FIG. 5 shows the effect of the SP2043 peptide (SEQ ID NO:1) on lymphatic endothelial cell (LEC) tube formation;

FIGS. 6A-6B shows the effect of the SP2043 peptide (SEQ ID NO:1) on hepatocyte growth factor (HGF) and insulin growth factor 1 (IGF1) signaling in vitro with microvascular endothelial cells (MEC; Panel A) and lymphatic endothelial cells (LEC; Panel B);

FIG. 7 shows the effect of the SP2043 peptide (SEQ ID NO:1) on the proliferation of triple-negative breast cancer cell lines MDA-MB-231 and SUM149, and the estrogen receptor positive cell line MCF-7;

FIG. 8 shows the effect of the SP2043 peptide (SEQ ID NO:1) on hepatocyte growth factor (HGF) signaling in MDA-MB-231 cells;

FIG. 9 shows the effect of the SP2043 peptide (SEQ ID NO:1) on the growth of MDA-MB-231 orthotopic tumors in SCID mice over 33 days (ip, intraperitoneal injection);

FIGS. 10A-10B show the effect of the SP2043 peptide (SEQ ID NO:1) (Panel B) on phosphorylation of c-Met and angiogenesis in vivo (Panel A, control);

FIGS. 11A-11G show the effect of the SP2043 peptide (SEQ ID NO:1) on angiogenesis as seen by lectin staining for immunohistochemistry (IHC) and LYVE-1 staining for lymphangiogenesis in vivo: control stained with lectin (Panel A) and LYVE-1 (Panel B); the SP2043 peptide (SEQ ID NO:1) stained with lectin (Panel C) and LYVE-1 (Panel D); control and the SP2043 peptide (SEQ ID NO:1) (Panel E); and pixel density using lectin (Panel F) and LYVE-1 (Panel G);

FIGS. 12A-12B show the effect of the SP2043 peptide (SEQ ID NO:1) on the metastasis of MDA-MB-231-luc tumors in multiple organs in the tumor-conditioned media pre-treated metastasis model by photon flux from tumor cells (Panel A) and the effect of the SP2043 peptide (SEQ ID NO:1) on the metastasis of MDA-MB-231-luc tumors to lymph nodes as seen by staining with vimentin antibody for the presence of human cells (Panel B);

FIGS. 13A-13E show the effect of the SP2043 peptide (SEQ ID NO:1) on neovascularization as compared to aflibercept in a CNV model (Panels A-B) and as compared to a control in a rho-VEGF mouse model (Panel C-E);

FIG. 14 shows the effect of the SP2043 peptide (SEQ ID NO:1) on the neovasculature in a laser induced CNV model in the mouse eye;

FIGS. 15A-15B show the effect of the SP2043 peptide (SEQ ID NO:1) on vascular leakage in the Tet/Opsin/VEGF mouse model;

FIG. 16 shows the effect of the SP2043 peptide (SEQ ID NO:1) on VEGF mediated vascular permeability in the rabbit eye;

FIG. 17 shows a representative example of SP2043 peptide (SEQ ID NO:1) loaded (2%) in poly(lactic-co-glycolic acid) (PLGA) microparticles; PLGA was used in a L:G ratio of 65/35, MW=40-75 kDa. Scale bar is 10 microns;

FIGS. 18A-18B show: (Panel A) 2% and 5% SP2043 peptide (SEQ ID NO:1) loaded PLGA microparticles and sizing; Number averaged particle distribution (Num. Avg) and volume averaged particle distribution (Vol. Avg) are indicated (Mean+SD); and (Panel B) the zeta potentials (surface charge) of 2% and 5% SP2043 peptide (SEQ ID NO:1) loaded microparticles;

FIGS. 19A and 19B show the controlled release of a labeled peptide analog of SP2043 from PLGA microparticles under physiological conditions in situ;

FIG. 20 shows the controlled release of the SP2043 peptide (SEQ ID NO:1) without any label or modification in PLGA microparticles in situ under physiological conditions (method shown in FIG. 32 below);

FIG. 21 shows SEM imaging of PLGA microparticles incorporating 2% by weight SP2043 (left) and 5% by weight 2043 (right). PLGA in this example used L:G ratio of 85/15, MW=190-240 kDa. Scale bar is 10 microns;

FIG. 22 shows the SP2043 peptide (SEQ ID NO:1) encapsulated into nanoparticles PLGA 65/35 was used. Ellipsoidal nanoparticles (left) and spherical nanoparticles (right);

FIG. 23 shows the effect of the PLGA 85/15 microparticle encapsulating the SP2043 peptide (SEQ ID NO:1) on regression in mouse eyes following laser-induced choroidal neovascularization in a mouse model (2 week data shown);

FIG. 24 shows the effect of PLGA 85/15 microparticles containing the SP2043 peptide (SEQ ID NO:1) on neovascularization overtime in a laser-induced wet AMD mouse model;

FIG. 25 shows the effect of PLGA 65/35 microparticles containing the SP2043 peptide (SEQ ID NO:1) on neovascularization overtime in a laser-induced wet AMD mouse model;

FIG. 26 shows the effect of the SP2043 peptide (SEQ ID NO:1) on the inhibition of neovascularization in a rabbit model. Data at day 34 following intravitreal injection into rabbit eyes;

FIG. 27 shows PLGA (85/15) encapsulating the SP2043 peptide (SEQ ID NO:1) in rho/VEGF transgenic mice;

FIG. 28 shows the effect of the SP2043 peptide (SEQ ID NO:1) in combination with other anti-angiogenesis agents in a laser-induced choroidal neovascularization model in mice;

FIG. 29 shows the effect of polymers, such as PBAEs, on the ability of the SP2043 peptide (SEQ ID NO:1) to self-assemble into approximately 100-nm nanoparticles. Polymer 447 refers to (3-aminopropyl)-4-methylpiperazine end-capped poly(1,4-butanediol diacrylate-co-4-amino-1-butanol) and polymer 657 refers to (3-aminopropyl)-4-methylpiperazine end-capped poly(1,6-hexanediol diacrylate-co-5-amino-1-pentanol) (B6-S5-E7). +/− refers to with or without the SP2043 peptide (SEQ ID NO:1). Particle size is larger and nanoparticle concentration larger when the SP2043 peptide (SEQ ID NO:1) is together with polymer for self-assembly;

FIG. 30 shows PLGA and PLGA-PEG nanoparticles encapsulating SP2043;

FIGS. 31A-31B show the effect of systemically intravenously injected SP2043 peptide (SEQ ID NO:1) containing nanoparticles or free peptide on accumulation in tumor, as well as other organs. FIG. 31A shows accumulation per organ and FIG. 31B shows total accumulation. In both figures, the term "naked" refers to the free peptide, while the terms "sphere," "ellipse," and "PEG," i.e., polyethylene glycol, refer to three different types of nanoparticles containing the SP2043 peptide (SEQ ID NO:1); and FIGS. 32A-32B show a method for quantifying the presently disclosed peptides by using electrophoresis and staining with SimplyBlue (Panel A) followed by mass spectrometry (Panel B). Panel A contained the following samples: lane 1, marker; lane 2, 4 μg SP2043 peptide (SEQ ID NO:1) positive control; lane 3, 4 μg SP2043 peptide (SEQ ID NO:1) in PBS medium; lane 4, 4 μg SP2043 peptide (SEQ ID NO:1) in FBS medium.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Mimetic Peptides Derived From Collagen Type IV

Peptides generally offer many advantages over other types of therapies for certain diseases in that they are non-immunogenic, less toxic because they bind to their targets with high specificity, and are inexpensive to produce. See, e.g., International PCT Patent Publication No. WO 2008/085828 and International PCT Patent Application Publication No. WO 2007/033215, each which is incorporated herein by reference in its entirety. The presently disclosed peptides exhibit anti-angiogenic, anti-vascular permeability, anti-tumorigenesis and/or anti-lymphangiogenic properties, which could lead to an increase in overall survival in certain diseases. For example, the presently disclosed peptides may benefit cancer patients and may help treat ocular proliferative diseases, such as age-related macular degeneration and diabetic retinopathy.

In general, the presently disclosed peptides are characterized by having the motif comprising the amino acid sequence LRRFSTXPXXXXDINDVXNF (SEQ ID No: 2). Peptides characterized by having the motif comprising the amino acid sequence LRRFSTXPXXXXNINNVXNF (SEQ ID No: 4) have been disclosed in International Publication WO 2012/079088 (incorporated herein by reference in its entirety). This motif was determined by making substitutions in the pentastatin-1 peptide. The WO 2012/079088 publication disclosed that, in some embodiments, the positions in SEQ ID No: 3 denoted by X could be varied and the resulting peptide could still be used for, and in some embodiments, was better for, inhibiting angiogenesis, lymphangiogenesis, vascular permeability and/or tumorigenesis, and for treatment of a subject thereof while other positions in SEQ ID No: 3 could not be varied to retain inhibitory characteristics. In other embodiments, it was found that X at the following positions could have the following substitutions in SEQ ID No: 3: position 7 could be M, A, or G; position 9 could be F, A, Y, or G; position 10 could be M, A, G, dA, or Nle; position 11 could be F, A, Y, G, or 4-ClPhe; position 12 and position 18 could be Abu, G, S, A, V, T, I, L or AllylGly. In an embodiment, the peptide characterized by having the motif comprising the amino acid sequence LRRFSTAPFAFININNVINF (SEQ ID No: 3; also called SP2036) was disclosed.

The presently disclosed peptides are characterized by having the motif comprising the amino acid sequence LRRFSTXPXXXXDINDVXNF (SEQ ID No: 2), which differs from previously disclosed SEQ ID No: 4 at positions 13 and 16 (Table 1). In a particular embodiment, a peptide characterized by having the motif comprising the amino acid sequence LRRFSTAPFAFIDINDVINF (SEQ ID No: 1; also called SP2043 and SEQ.1) is disclosed which differs from previously disclosed SEQ ID No: 3 (also called SP2036) at positions 13 and 16 (Table 1). It is disclosed herein that the substitution of aspartate at positions 13 and 16 results in a peptide that is less hydrophobic, but still can be used for inhibiting angiogenesis, lymphangiogenesis, vascular permeability and/or tumorigenesis involving a cell, tissue, or organ, and for treatment of a subject thereof. Further, because this peptide is less hydrophobic, it is easier to produce.

TABLE 1

Representative Peptides

| | | | | | | |
|---|---|---|---|---|---|---|
| SEQ ID NO: 1 | LRRFST | A P | FAFI | DINDV | INF | SP2043 |
| SEQ ID NO: 2 | LRRFST | X P | XXXX | DINDV | XNF | |
| SEQ ID NO: 3 | LRRFST | A P | FAFI | NINNV | INF | SP2036 |
| SEQ ID NO: 4 | LRRFST | X P | XXXX | NINNV | XNF | |

A. Representative Embodiments

In a particular embodiment, the isolated peptide comprises the amino acid sequence LRRFSTAPFAFIDINDVINF (SEQ ID NO: 1).

In some embodiments, the peptide comprises the amino acid sequence LRRFSTXPXXXXDINDVXNF (SEQ ID NO: 2), and wherein X is any amino acid. X may be a natural or non-natural amino acid.

In other embodiments, the peptide comprises the amino acid sequence LRRFSTXPXXXXDINDVXNF (SEQ ID NO:2), wherein X at position 7 is M, A, or G; X at position 9 is F, A, Y, or G; X at position 10 is M, A, G, dA, or Nle; X at position 11 is F, A, Y, G, or 4-C1Phe; X at position 12 and position 18 are Abu, G, S, A, V, T, I, L or AllyGly. Each substitution at an X residue in this embodiment has either been tested (as shown in International PCT Patent Application Publication No. WO 2012/079088, which is incorporated herein by reference in its entirety, or in the Examples provided herein below) or is a conservative amino acid substitution for a tested amino acid.

In some embodiments, the presently disclosed peptides have several X residues that may be any amino acid, whether natural or non-natural (X7, X9, X10, X11, X12, and X18). By natural amino acids, it is meant those amino acids that occur in nature, such as glycine, alanine, valine, leucine, isoleucine, serine, threonine, aspartic acid, asparagine, lysine, glutamic acid, glutamine, arginine, histidine, phenylalanine, cysteine, tryptophan, tyrosine, methionine, proline, pyrrolysine, and selenocysteine. By non-natural amino acids, it is meant amino acids that do not occur in nature, but that can be incorporated into a polypeptide chain. Non-natural amino acids include, but are not limited to 2-aminobutyric acid (Abu), norleucine (Nle), 4-chloro phenylalanine (4-C1Phe), allylglycine (AllyGly) and other non-natural amino acids such as those detailed in Ma (2003). Amino acid analogs that are known in the art may be employed in the presently disclosed subject matter.

A "peptide" or "protein" comprises a string of at least three amino acids linked together by peptide bonds. The terms "protein" and "peptide" may be used interchangeably. Peptide may refer to an individual peptide or a collection of peptides. Also, one or more of the amino acids in a presently disclosed peptide may be modified, for example, by the addition of a chemical entity such as a carbohydrate group, a phosphate group, a farnesyl group, an isofarnesyl group, a fatty acid group, a linker for conjugation, functionalization, or other modification, and the like. In some embodiments, the modifications of the peptide lead to a more stable peptide (e.g., greater half-life in vivo). In other embodiments, other modifications may include cyclization of the peptide, the incorporation of D-amino acids, other molecules conjugated to the N-terminus and C-terminus, conjugation of fluorescent probes, biomolecules, such as poly(ethylene glycol), targeting ligands, and the like, retro-inversion and the like. None of the modifications should substantially interfere with the desired biological activity of the peptide.

By "Collagen IV derived peptide" it is meant a peptide comprising a C-N-X(3)-V-C or P-F-X(2)-C or LX(2)FX(3)PFX(2)CNX(4)CNX collagen motif. If desired, the peptide includes at least about 5, 10, 20, 30, 40, 50 or more amino acids that flank the carboxy or amino terminus of the motif in the naturally occurring amino acid sequence. Type IV collagen derived peptides include, for example, pentastatin-1, tumstatin, and targeting RGD. By "alteration" is meant a change in the sequence or in a modification (e.g., a post-translational modification) of a gene or polypeptide relative to an endogeneous wild-type reference sequence.

By an "isolated peptide" is meant a presently disclosed peptide that has been separated from components that naturally accompany it. Typically, the peptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a presently disclosed peptide. An isolated peptide may be obtained, for example, by extraction from a natural source, by expression of a recombinant nucleic acid encoding such a peptide; or by chemically synthesizing the protein. Purity can be measured by any appropriate method, for example, column chromatography, polyacrylamide gel electrophoresis, or by HPLC analysis.

By "substantially identical" is meant a peptide, a polypeptide or nucleic acid molecule exhibiting at least 50% identity to a reference amino acid sequence (for example, any one of the amino acid sequences described herein) or nucleic acid sequence. Preferably, such a sequence is at least 60%, more preferably 80% or 85%, and even more preferably 90%, 95% or even 99% identical at the amino acid level or nucleic acid to the sequence used for comparison.

"Functional variants" of SEQ ID NO:1 and SEQ ID NO:2 include functional fragments and/or functional fusion peptides. A functional variant of the presently disclosed sequences refers to an isolated and/or recombinant peptide which has at least one property, activity and/or function characteristic of peptide encoded by SEQ ID NO:1 or SEQ ID NO:2, such as exhibiting anti-angiogenic, anti-vascular permeability, anti-tumorigenesis and/or anti-lymphangiogenic properties, which could lead to an increase in overall survival in certain diseases. Generally, fragments or portions of the presently disclosed peptides encompassed by the presently disclosed subject matter include those having a deletion (i.e., one or more deletions) of an amino acid (i.e., one or more amino acids) relative to the peptides encoded by SEQ ID NO: 1 or SEQ ID NO: 2 (such as N-terminal, C-terminal or internal deletions). Fragments or portions in which only contiguous amino acids have been deleted or in which non-contiguous amino acids have been deleted are also envisioned. Generally, mutants or derivatives of the presently disclosed peptides include natural or artificial variants differing by the addition, deletion and/or substitution of one or more contiguous or non-contiguous amino acid residues, or modified peptides in which one or more residues is modified, and mutants comprising one or more modified residues.

Generally, a functional variant of SEQ ID NO: 1 or SEQ ID NO:2 thereof has an amino acid sequence which is at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to SEQ ID NO:1 or SEQ ID NO:2 over the length of the variant.

Generally, an amino acid sequence that has percent identity to the presently disclosed sequences has at least about 80% identical, at least about 81% identical, at least about 82% identical, at least about 83% identical, at least about 84% identical, at least about 85% identical, at least about 86% identical, at least about 87% identical, at least about 88% identical, at least about 89% identical, at least about 90% identical, at least about 91% identical, at least about 92% identical, at least about 93% identical, at least about 94% identical, at least about 95% identical, at least about 96% identical, at least about 97% identical, at least about 98% identical, or at least about 99% identical to the presently disclosed sequences over the length of the variant.

In some embodiments, the presently disclosed subject matter provides an isolated peptide comprising an amino acid sequence at least 85% identical to LRRFSTAPFAFIDINDVINF (SEQ ID NO: 1), wherein the peptide exhibits anti-angiogenic, anti-vascular permeability, anti-tumorigenesis and/or anti-lymphangiogenic properties. In other embodiments, the presently disclosed subject matter provides a composition comprising a pharmaceutically acceptable carrier and an effective amount of the isolated peptide comprising an amino acid sequence at least 85% identical to LRRFSTAPFAFIDINDVINF (SEQ ID NO: 1), wherein the peptide exhibits anti-angiogenic, anti-vascular permeability, anti-tumorigenesis and/or anti-lymphangiogenic properties. In further embodiments, the presently disclosed subject matter provides a kit comprising an isolated peptide comprising an amino acid sequence at least 85% identical to LRRFSTAPFAFIDINDVINF (SEQ ID NO: 1), wherein the peptide exhibits anti-angiogenic, anti-vascular permeability, anti-tumorigenesis and/or anti-lymphangiogenic properties. In still further embodiments, the presently disclosed subject matter provides a nanoparticle or microparticle comprising an isolated peptide comprising an amino acid sequence at least 85% identical to LRRFSTAPFAFIDINDVINF (SEQ ID NO: 1), wherein the peptide exhibits anti-angiogenic, anti-vascular permeability, anti-tumorigenesis and/or anti-lymphangiogenic properties.

Further, the presently disclosed peptides can be modified to make them less susceptible to proteolysis. For example, they can be truncated to the minimal potent sequence. Such truncation is important to limit binding to other receptors that would dilute the effective concentration, as well as lead to unexpected side effects. Such truncation also opens up the possibility to create a single multimodal peptide out of multiple short peptides, each of which targets angiogenesis, lymphangiogenesis and tumorigenesis by a different mechanism. Multimodal treatment is very important to reduce the incidence of drug resistance, because it is less likely that the tumor will be able to mount a successful resistance when attacked simultaneously from multiple fronts.

In addition, the presently disclosed peptides with different sequences can be used together in one composition or method. There may be compositions or methods where multiple types of the presently disclosed peptides allow better prevention or reduction of angiogenesis, vascular permeability, tumorigenesis and/or lymphangiogenesis. Therefore, instead of a composition with a single multimodal peptide, a composition may be comprised of multiple types of isolated peptides that are not covalently bound together.

Further, in some embodiments, the presently disclosed peptides are tri-fluoro acetate (TFA) salts. For use in humans, however, the TFA salts can be modified to acetate salts or other pharmaceutically acceptable salts.

The term "pharmaceutically acceptable salts" is meant to include salts of active compositions which are prepared with relatively nontoxic acids or bases, depending on the particular substituent moieties found on the compositions described herein. When compositions of the present disclosure contain relatively acidic functionalities, base addition salts can be obtained by contacting the neutral form of such compositions with a sufficient amount of the desired base, either neat or in a suitable inert solvent. Examples of pharmaceutically acceptable base addition salts include sodium, potassium, calcium, ammonium, organic amino, or magnesium salt, or a similar salt. When compositions of the present disclosure contain relatively basic functionalities, acid addition salts can be obtained by contacting the neutral form of such compositions with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science, 1977, 66, 1-19). Certain specific compositions of the present disclosure contain both basic and acidic functionalities that allow the compositions to be converted into either base or acid addition salts.

In addition, it is possible to increase the half-lives of the peptides by conjugating the peptides to certain compositions. For example, it is possible to conjugate the peptides to catalytic antibodies or to polymers, such as polyethylene glycol (PEG), to increase their half-lives and/or promote self-assembly into particles.

In some embodiments, the presently disclosed subject matter provides a composition comprising a pharmaceutically acceptable carrier and an effective amount of a presently disclosed peptide, or a functional variant thereof. In other embodiments, the presently disclosed subject matte provides a kit comprising a presently disclosed isolated peptide, or a functional variant thereof. The amount of peptide can vary widely, but generally the amount is sufficient to perform at least one of the presently disclosed methods.

As used herein, "pharmaceutically acceptable carrier" is intended to include, but is not limited to, water, saline, dextrose solutions, human serum albumin, liposomes, hydrogels, microparticles and nanoparticles. The use of such media and agents for pharmaceutically active compositions is well known in the art, and thus further examples and methods of incorporating each into compositions at effective levels need not be discussed here. Such compositions also can include coatings, antibacterial and/or fungal agents, and any other ingredient that is biologically tolerable.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

In general, a presently disclosed kit contains some or all of the components, reagents, supplies, and the like to practice a method according to the presently disclosed subject matter. In a kit comprising an isolated peptide or a functional variant thereof according to the presently disclosed subject matter, the kit typically comprises an effective amount of peptide to prevent, delay, reduce, or treat a disease related to angiogenesis, lymphangiogenesis, vascular permeability, and/or tumorigenesis. In one embodiment, a kit comprises at least one container (e.g. a vial, tube, or ampoule) comprising an isolated peptide of the presently disclosed subject matter. Typically, the isolated peptide or peptides will be supplied in one or more container, each container containing an effective amount of isolated peptide to allow a change in angiogenesis, lymphangiogenesis, vascular permeability, and/or tumorigenesis to occur.

B. Representative Biodegradable Delivery Platforms

In some embodiments, the presently disclosed peptides are effective when loaded onto or into, or otherwise associated with, nano- or microparticles. Accordingly, in come embodiments, the presently disclosed subject matter provides a nanoparticle or microparticle comprising a presently disclosed peptide, or a functional variant thereof.

In particular embodiments, the nanoparticle or microparticle comprises poly(lactic-co-glycolic acid) (PLGA) and/or PLGA-polyethylene glycol (PEG). In some embodiments, about 2% to about 5% by mass of the isolated peptide is loaded onto or into PLGA and/or PLGA-PEG nanoparticles or microparticles. In yet other embodiments, about 6% to about 10% by mass of the isolated peptide is loaded onto or into the PLGA and/or PLGA-PEG nanoparticles or microparticles.

Further, in other embodiments, certain polymer formulations, microparticles, nanoparticles, and the like, which are suitable for use with the presently disclosed subject matter are disclosed in International PCT Patent Application Publication No. WO/2012/0128782 for "Multicomponent Degradable Cationic Polymers," International PCT Patent Application Publication No. WO/2012/0114759 for "Peptide/Particle Delivery Systems," International PCT Patent Application Publication No. WO/2014/066811 for "Bioreducible Poly(beta-amino ester)s for siRNA Delivery," and International PCT Patent Application Publication No. WO/2014/066898 for "A Layer-by-Layer Approach to Codeliver DNA and siRNA via AuNPs: A Potential Platform for Modifying Release Kinetics," all to Green et al., and each of which is incorporated herein by reference in its entirety.

As used herein, the term "poly(beta-amino ester) (PBAE)" can refer to a compound of the general formula:

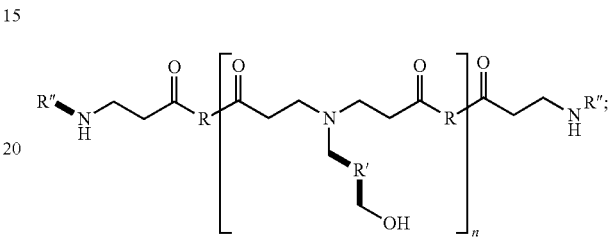

wherein:
n is an integer from 1 to 10,000;
R comprises a backbone of a diacrylate selected from the group consisting of:

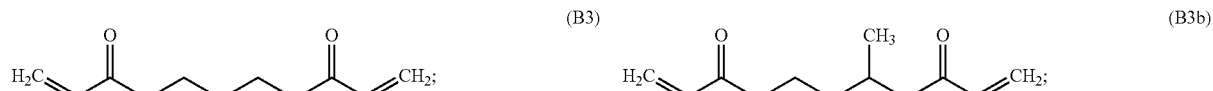

(B3) (B3b)

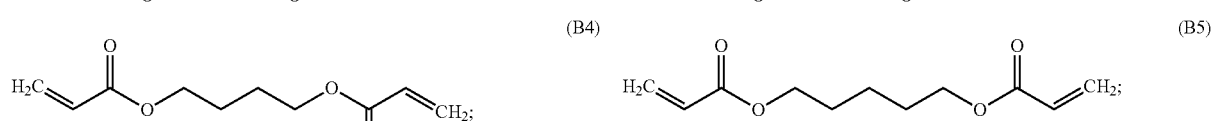

(B4) (B5)

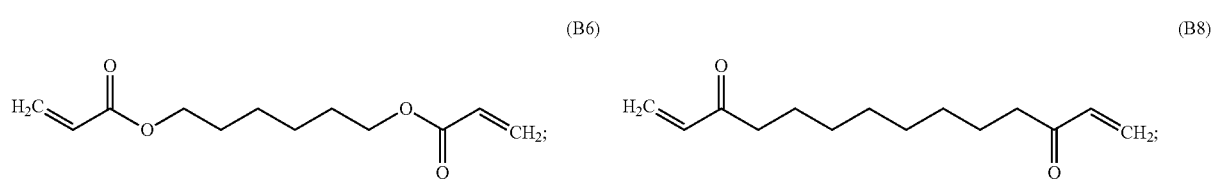

(B6) (B8)

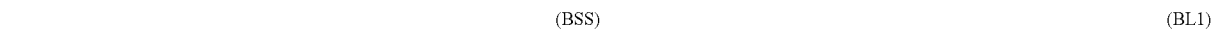

(BSS) (BL1)

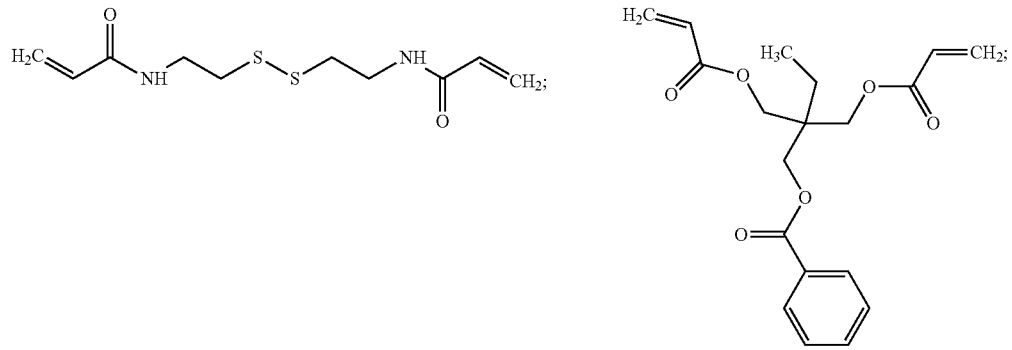

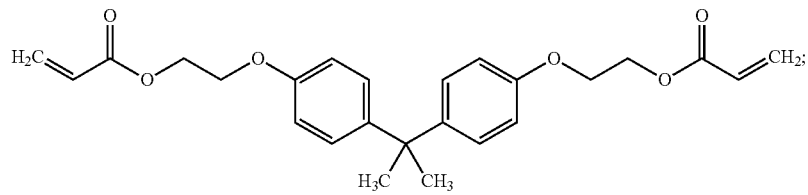
(BL2)
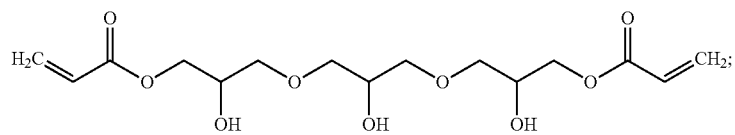
(BH1)
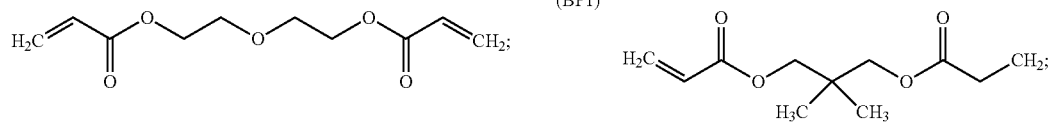
(BP1) (BP2)
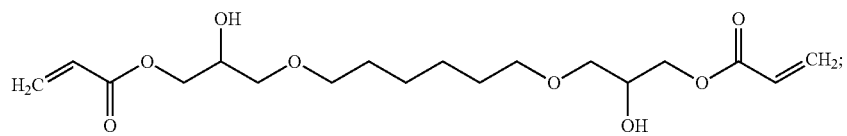
(BP3)
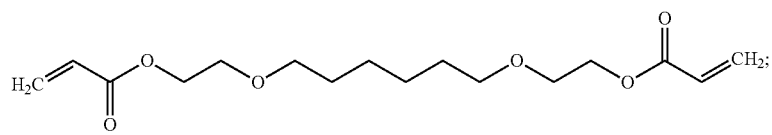
(BP4)
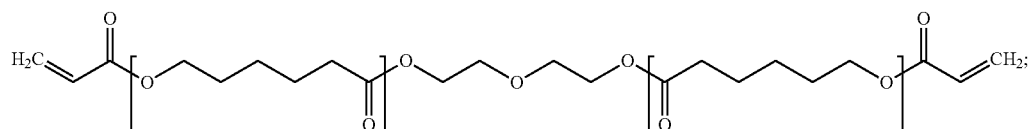
(BP6)
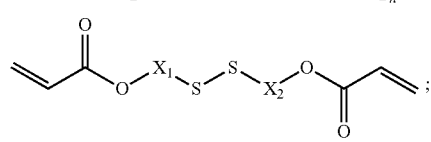
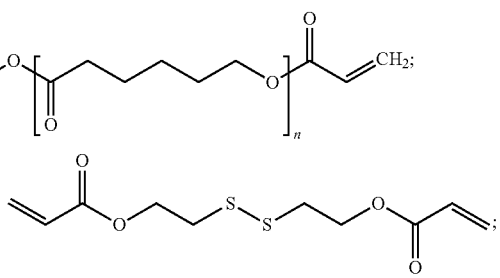
2,2′-disulfanediylbis(ethane-2,1-diyl) diacrylate
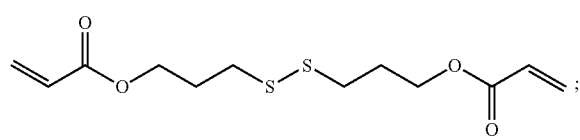
disulfanediylbis(propane-3,1-diyl) diacrylate
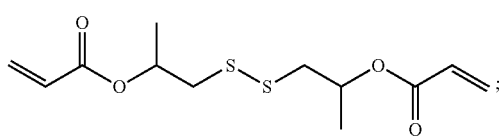
disulfanediylbis(propane-2,1-diyl) diacrylate
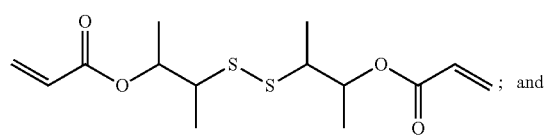
disulfanediylbis(butane-3,2-diyl) diacrylate
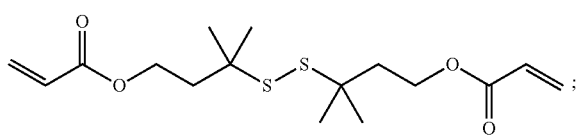
disulfanediylbis(3-methylbutane-3,1-diyl) diacrylate R' comprises a side chain derived from a compound selected from the group consisting of:

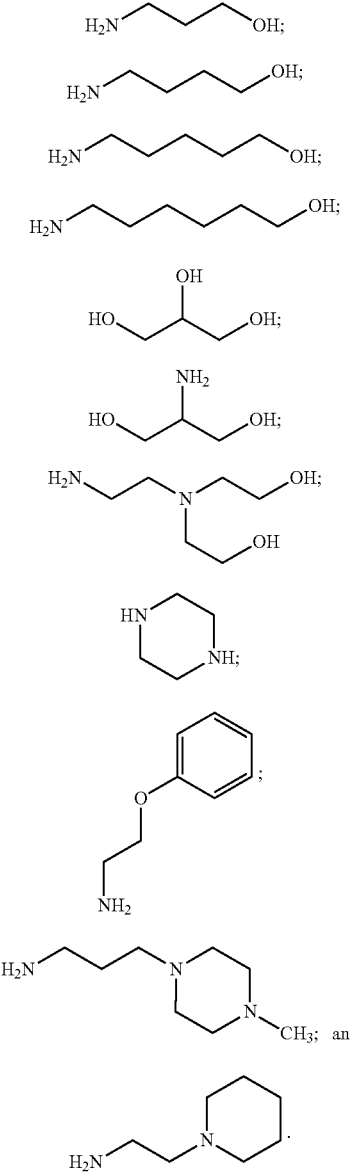

R" comprises an end group derived from a compound selected from the group consisting of

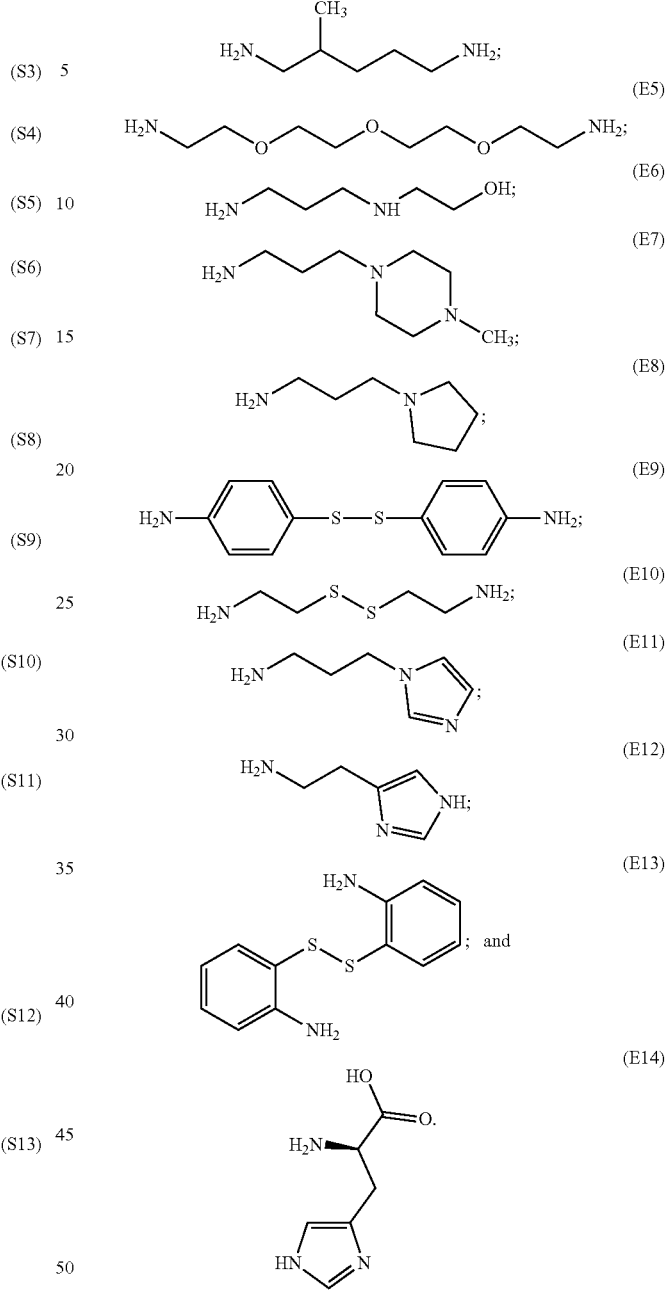

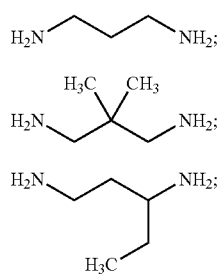

In such embodiments, the polymer compositions can be designated as, for example, B6-S5-E7 or 657, in which R is B6, R' is S5, and R" is E7.

Accordingly, in some embodiments, the nanoparticle or microparticle comprises a poly(beta-amino ester) (PBAE) and/or PBAE-PEG. In particular embodiments, the nanoparticle or microparticle comprises about 1% to about 5% by mass of the isolated peptide loaded onto or into the PBAE and/or PBAE-PEG nanoparticles or microparticles. In yet other embodiments, the nanoparticle or microparticle comprises about 6% to about 10% by mass of the isolated peptide loaded onto or into the PBAE and/or PBAE-PEG nanoparticles or microparticles.

In yet other embodiments, the nanoparticle or microparticle comprises a combination of a poly(beta-amino ester)

(PBAE), PLGA, and PEG. In particular embodiments, the nanoparticle or microparticle comprises about 1% to about 5% by mass of the isolated peptide loaded onto or into particles comprising a combination of a poly(beta-amino ester) (PBAE), PLGA, and PEG. In still other embodiments, the nanoparticle or microparticle comprises about 6% to about 10% by mass of the isolated peptide loaded onto or into particles comprising a combination of a poly(beta-amino ester) (PBAE), PLGA, and PEG.

As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 µm). In such embodiments, the particle also can be referred to as a "microparticle". Thus, the term "microparticle" includes particles having at least one dimension in the range of about one micrometer (µm), i.e., $1\times10^{-6}$ meters, to about 1000 µm. The term "particle" as used herein is meant to include nanoparticles and microparticles. In some embodiments, the microparticle is between 1-5 µm. In other embodiments, the microparticle is 3-10 µm. In some other embodiments, the microparticle is 10-20 µm. In further embodiments, the microparticles and nanoparticles are spherical in shape. In still further embodiments, the microparticles and nanoparticles have a non-spherical shape. In some embodiments, the particles have an ellipsoidal shape with an aspect ratio of the long axis to the short axis between 2 and 10.

In some embodiments, the three-dimensional microparticle or nanoparticle comprises a material having one or more of the following characteristics: (i) one or more degradable linkages; (ii) a stretchable modulus; and (iii) a glass transition temperature such that the material comprising the three-dimensional microparticle or nanoparticle is a solid at room temperature and/or body temperature. In other embodiments, the degradable linkage is selected from the group consisting of an ester linkage, a disulfide linkage, an amide linkage, an anhydride linkage, and a linkage susceptible to enzymatic degradation.

In particular embodiments, the microparticle or nanoparticle comprises a biodegradable polymer or blends of polymers selected from the group consisting of poly(lactic-co-glycolic acid) (PLGA), poly(beta-amino ester) (PBAE), polycaprolactone (PCL), polyglycolic acid (PGA), polylactic acid (PLA), poly(acrylic acid) (PAA), poly-3-hydroxybutyrate (P3HB) and poly(hydroxybutyrate-co-hydroxyvalerate). In other embodiments, nondegradable polymers that are used in the art, such as polystyrene, are blended with a degradable polymer or polymers from above to create a copolymer system. Accordingly, in some embodiments, a nondegradable polymer is blended with the biodegradable polymer.

As used herein, "biodegradable" compositions are those that, when introduced into cells, are broken down by the cellular machinery or by hydrolysis into components that the cells can either reuse or dispose of without significant toxic effect on the cells (i.e., fewer than about 20% of the cells are killed when the components are added to cells in vitro). The components preferably do not induce inflammation or other adverse effects in vivo. In certain preferred embodiments, the chemical reactions relied upon to break down the biodegradable compositions are uncatalyzed.

In some other embodiments, the microparticle or nanoparticle is biocompatible. The term "biocompatible", as used herein is intended to describe compositions that are not toxic to cells. Compositions are "biocompatible" if their addition to cells in vitro results in less than or equal to 20% cell death, and their administration in vivo does not induce inflammation or other such adverse effects.

It will be appreciated by one of ordinary skill in the art that nanoparticles and microparticles suitable for use with the presently disclosed methods can exist in a variety of shapes, including, but not limited to, spheroids, rods, disks, pyramids, cubes, cylinders, nanohelixes, nanosprings, nanorings, rod-shaped particles, arrow-shaped particles, teardrop-shaped particles, tetrapod-shaped particles, prism-shaped particles, and a plurality of other geometric and non-geometric shapes.

C. General Terms

For clarity, other general terms are described below. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

"Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins it is recognized that residue positions which are not identical often differ by conservative amino acid substitutions, where amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences that differ by such conservative substitutions are said to have sequence similarity. Approaches for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers and Miller, *Computer Applic. Biol. Sci.*, 4: 11-17, 1988, for example, as implemented in the program PC/GENE (Intelligenetics, Mountain View, Calif., USA).

"Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "homologous" in their various grammatical forms in the context of polynucleotides means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 85%, 90%, and even more preferably at least 95%.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 5, 10, or 15 amino acids, preferably at least about 20 amino acids, more preferably at least about 25 amino acids, and even more preferably about 35 amino acids, about 50 amino acids, about 100 amino acids, or about 150 amino acids.

II. Methods of Treating Angiogenesis—and Lymphangiogenesis-Dependent Diseases

A. Representative Embodiments

In some embodiments, the presently disclosed peptides exhibit anti-angiogenic anti-lymphangiogenic, anti-tumorigenic, and/or anti-vascular permeability properties. Angiogenesis refers to the growth of new blood vessels originating from existing blood vessels. Lymphangiogenesis refers to the formation of lymphatic vessels de novo or from preexisting lymphatic vessels, in a method believed to be similar to blood vessel development or angiogenesis. Tumorigenesis refers to the formation of a tumor. Vascular permeability refers to the property of blood microvascular walls including blood capillary walls that allows for the selective exchange of substances.

In some embodiments, the presently disclosed subject matter provides a method for inhibiting angiogenesis, lymphangiogenesis, vascular permeability and/or tumorigenesis involving a cell. The method comprises contacting a cell with a presently disclosed isolated peptide or a functional variant thereof in an amount sufficient to inhibit angiogenesis, lymphangiogenesis, vascular permeability and/or tumorigenesis of the cell. The contacting of the cell may result in an inhibition of adhesion, migration, proliferation, and/or tube formation involving the cell. In a particular embodiment, the cell is an endothelial cell.

In other embodiments, the method for inhibiting angiogenesis, lymphangiogenesis, vascular permeability and/or tumorigenesis involving a cell comprises: contacting the cell with an isolated peptide comprising an amino acid sequence at least 85% identical to LRRFSTAPFAFIDINDVINF (SEQ ID NO: 1), in an amount sufficient to inhibit angiogenesis, lymphangiogenesis, vascular permeability and/or tumorigenesis involving the cell. In further embodiments, contacting the cell results in an inhibition of adhesion, migration, proliferation, and/or tube formation involving the cell. In a particular embodiment, the cell is selected from the group consisting of an endothelial cell, a microvascular cell, and a lymphatic cell. In other embodiments, the cell is found in adipose tissue and the method reduces or prevents obesity. In still other embodiments, the cell is a transplanted cell and the method reduces or prevents tissue and/or organ rejection after transplantation of the cell. By "transplantation of the cell", it is meant that the cell is moved from one body to another body.

In some embodiments, the isolated peptide is loaded onto or into a nanoparticle or microparticle before contacting the cell. In other embodiments, the nanoparticle or microparticle comprises PLGA and/or PLGA-PEG.

The methods of the presently disclosed subject matter can be practiced in vivo as either a therapeutic method for treating a disease or disorder involving angiogenesis, lymphangiogenesis, vascular permeability and/or tumorigenesis or as a prophylactic method to prevent angiogenesis, lymphangiogenesis, vascular permeability and/or tumorigenesis. Likewise, the method can be practiced in vitro as a research tool to study the effects of angiogenesis, lymphangiogenesis, vascular permeability and/or tumorigenesis on a cell. The method also can be practiced ex vivo for therapeutic or research purposes.

"Contacting" means any action that results in at least one isolated peptide of the presently disclosed subject matter physically contacting at least one cell. It thus may comprise exposing the cell(s) to the isolated peptide in an amount sufficient to result in contact of at least one isolated peptide with at least one cell. The method can be practiced in vitro or ex vivo by introducing, and preferably mixing, the isolated peptide and cells in a controlled environment, such as a culture dish or tube. The method can be practiced in vivo, in which case contacting means exposing at least one cell in a subject to at least one isolated peptide of the presently disclosed subject matter, such as administering the isolated peptide to a subject via any suitable route. According to the presently disclosed subject matter, contacting may comprise introducing, exposing, and the like, the isolated peptide at a site distant to the cells to be contacted, and allowing the bodily functions of the subject, or natural (e.g., diffusion) or man-induced (e.g., swirling) movements of fluids to result in contact of the isolated peptide and cell(s).

In some embodiments, the presently disclosed subject matter provides a method for treating a subject suffering from a disease related to angiogenesis, lymphangiogenesis, vascular permeability and/or tumorigenesis, or to prevent or delay a subject from developing a disease related to angiogenesis, lymphangiogenesis, vascular permeability and/or tumorigenesis, the method comprising: administering to the subject a presently disclosed isolated peptide, or a functional variant thereof, in an amount sufficient to treat, delay, or prevent the disease in the subject.

In particular embodiments, the presently disclosed subject matter provides a method for treating a subject suffering from a disease related to angiogenesis, lymphangiogenesis, vascular permeability, and/or tumorigenesis or to prevent or delay a subject from developing a disease related to angiogenesis, lymphangiogenesis, vascular permeability, and/or tumorigenesis, the method comprising: administering to the subject an isolated peptide comprising an amino acid sequence at least 85% identical to LRRFSTAPFAFIDIND-VINF (SEQ ID NO: 1), in an amount sufficient to treat, delay, or prevent the disease in the subject.

In some embodiments, the subject is human. In other embodiments, the subject is nonhuman.

Representative diseases include those diseases that are angiogenesis-, lymphangiogenesis-, tumorigenesis-, and or vascular permeability-dependent. Accordingly, in some embodiments, the disease is a cancer. In other embodiments, the cancer is selected from the group consisting of breast, lung, glioblastoma, renal cell, hepatic cell, head, and neck cancer. In still other embodiments, the method inhibits angiogenesis, lymphangiogenesis, vascular permeability, and/or tumorigenesis in or surrounding a tumor. In further embodiments, the tumor is a primary tumor or an established metastasized tumor. In still further embodiments, the method inhibits the establishment of metastatis or inhibits further metastasis of the cancer. In other embodiments, the method inhibits dissemination of tumor cells through the blood and/or lymphatic vasculature.

In some embodiments, the method inhibits lymphangiogenesis, angiogenesis and/or tumorigenesis perioperatively to reduce or prevent tumor regrowth and metastasis. In other embodiments, the method inhibits lymphangiogenesis, angiogenesis and/or tumorigenesis postoperatively, after surgical complete or partial excision of the primary tumor, thereby reducing or preventing tumor regrowth and metastasis. Therefore, in some embodiments, the method inhibits lymphangiogenesis, angiogenesis and/or tumorigenesis perioperatively and/or postoperatively.

In still further embodiments, the method inhibits lymphangiogenesis, thereby reducing or preventing tissue and organ rejection after transplantation, e.g., with skin grafts, bone grafts, and other tissues and organs.

In some embodiments, the method inhibits angiogenesis and/or lymphangiogenesis in adipose tissue thereby reducing or preventing obesity.

In some embodiments, the disease is related to ocular angiogenesis or diabetic retinopathy. In other embodiments, the disease is selected from the group consisting of age-related macular degeneration, macular edema, neovascular glaucoma, proliferative diabetic retinopathy, and retinopathy of prematurity.

In further embodiments, the isolated peptide is loaded into or onto a nanoparticle or microparticle before administering to the subject. In still further embodiments, the nanoparticle or microparticle comprises PLGA and/or PLGA-PEG. In other embodiments, about 2% to about 5% by mass of the isolated peptide is loaded onto or into PLGA nanoparticles or microparticles. In yet other embodiments, about 6% to about 10% by mass of the isolated peptide loaded onto or into the PLGA and/or PLGA-PEG nanoparticles or microparticles.

In some embodiments, the isolated peptide is administered in combination with at least one other anti-angiogenesis agent. In particular embodiments, the at least one other anti-angiogenesis agent is selected from the group consisted of aflibercept, ranibizumab, bevacizumab, and combinations thereof. In certain embodiments, the presently disclosed subject matter provides for the use of the isolated peptides in the treatment of a disease associated with angiogenesis, lymphangiogenesis, tumorigenesis, and/or vascular permeability. The use is in particular for in vivo therapeutic or prophylactic methods of inhibiting angiogenesis, lymphangiogenesis, tumorigenesis, and/or vascular permeability. Certain embodiments provide for the use of the isolated peptides in the preparation of compositions for medical use, such as pharmaceutical or therapeutic compositions. In general, use of the isolated peptides is in combining them with other substances to make medicinal compositions.

The peptides according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

B. General Terms

By "disease" is meant any condition, dysfunction or disorder that damages or interferes with the normal function of a cell, tissue, or organ.

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells.

By "blood vessel formation" is meant the dynamic process that includes one or more steps of blood vessel development and/or maturation, such as angiogenesis, vasculogenesis, formation of an immature blood vessel network, blood vessel remodeling, blood vessel stabilization, blood vessel maturation, blood vessel differentiation, or establishment of a functional blood vessel network.

By "vasculogenesis" is meant the development of new blood vessels originating from stem cells, angioblasts, or other precursor cells.

By "blood vessel stability" is meant the maintenance of a blood vessel network.

By "neoplasia" is meant a disease that is caused by or results in inappropriately high levels of cell division, inappropriately low levels of apoptosis, or both. Solid tumors, hematological disorders, and cancers are examples of neoplasias.

A "tumor," as used herein, refers to all neoplastic cell growth and proliferation, whether malignant or benign, and all precancerous and cancerous cells and tissues.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduce" is meant a decrease in a parameter (e.g., blood vessel formation) as detected by standard art known methods, such as those described herein. As used herein, reduce includes a 10% change, preferably a 25% change, more preferably a 40% change, and even more preferably a 50% or greater change.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In therapeutic and/or diagnostic applications, the compositions of the disclosure can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000). To aid in bioavailability, the compositions of the disclosure may be delivered in a nano- or micro-particles.

Pharmaceutically acceptable salts are generally well known to those of ordinary skill in the art, and may include, by way of example, but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000). Pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compositions herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compositions can be formulated readily using pharmaceutically acceptable carriers well known in the art into dosages suitable for oral administration. Such carriers enable the compositions of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compositions into preparations which can be used pharmaceutically. The preparations formulated for oral administration may be in the form of tablets, dragees, capsules, or solutions.

Pharmaceutical preparations for oral use can be obtained by combining the active compositions with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (scC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compositions may be dissolved or suspended in suitable liquids, such as fatty oils, liquid paraffin, or liquid polyethylene glycols (PEGs). In addition, stabilizers may be added.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Materials and Methods

Growth of Cells in Cell Culture. For the growth of cells in cell culture, human umbilical vein endothelial cells (HUVEC), microvascular endothelial cells (MEC), and lymphatic endothelial cells (LEC) were purchased from Lonza and maintained according to the manufacturer's recommendation using Endothelial Basal Media (EBM-2) supplemented with the Bullet Kit (EGM-2, Lonza). The MEC and LEC were propagated in Microvascular Endothelial Cell Growth Medium-2 (EGM-2MV, Lonza). Breast cancer cells, MDA-MB-231 were supplied by Dr. Zaver Bhujwalla (JHMI, Radiology and Oncology). The cells were propagated in RPMI-1640 medium (Gibco, Carlsbad, CA) supplemented with 10% FBS and antibiotics (1% penicillin/streptomycin). Cells were maintained under standard conditions of 37° C. and 5% $CO_2$ and the passage numbers of all used cells were between 2 and 7.

Peptide Synthesis. Peptides were synthesized using solid state synthesis and were supplied as TFA salts with an amidated C-terminus and an amine at the N-terminus (New England Peptide, Gardner, MA). The purity of the peptides was >95% and the suppliers provided product characterization (MALDI-TOF, HPLC/MS, and HPLC traces) as proof of MW and purity accuracy. Peptides were solubilized in 5% DMSO and water due to their hydrophobic profile. The pH of solubilized peptides was checked and found to be around pH 7. For all experiments the DMSO % was maintained at non-toxic threshold (determined by toxicity curves of DMSO on cells) with a final DMSO percentage (<0.2%), which was used as control in all experiments.

Proliferation Assay. A colorimetric based proliferation assay using WST-1 (Roche, 11644807001) proliferation reagent was carried out using HREC cells, HUVEC cells, and the breast cancer cells MDA-MB-231, MCF-7, and SUM149. 2000 cells/well were plated in 96-well plates and allowed to adhere overnight. On the following day, the media was exchanged with fully supplemented media containing peptides or equivalent DMSO vehicle for the controls. Three days later, the media containing the peptides was replaced with serum-free EBM-2 media containing WST-1 reagent and the plates were incubated for four hours as per the manufacturer's recommendations. Changes in color, due to the formazan dye resulted from the cleavage of the tetrazolium salt WST-1 by the mitochondrial succinate-tetrazolium reductase, were read on a Victor V fluorescence plate reader (Perkin Elmer, MA) by measuring the absorbance at 450 nm. Dose response curves of percent live cells (in comparison to untreated cells, but incubated in complete media with 0.2% DMSO) were created. Assays were performed in at least two independent replicates and each replicate was performed using three experimental triplicates.

Migration Assay. The inhibitory potential of the peptides was measured using a real time migration assay system based on electrical impedance (RT-CIM, ACEA Biosciences, CA). CIM 16 well plates (Roche, 05665817001) are composed of a top and bottom chamber separated by a microporous (8 μm) polycarbonate membrane. The membrane was coated with fibronectin (20 μg/mL), and 45,000 cells/well in serum free media with or without peptides were added to the top compartment. Media with chemoattractant (i.e., fully supplemented EBM-2) was added to the bottom compartment of the chamber and the plate was incubated at 37° C. for 20 hours. The sensors integrated on the bottom side of the membrane monitor and continuously record changes in impedance as the cells move through the membrane. The RT-CIM technology allows for easy quantification of cell migration by monitoring the cell index derived from the measured impedances. Assays were performed in at least two independent replicates and each replicate was performed using two experimental duplicates. Breast cancer cells MDA-MB-231 are not suitable for the RT-CIM type experiments due to their thin elongated phenotype, thus the inhibition of migration was investigated using a wound healing type assay. This assay was performed using the Oris Pro Migration assay (Platypus Technologies, CMA 1.101). Briefly, 25,000 cells/well in full media were added to the 96 well plate containing stoppers to block migration of cells to the center region of the wells. Cells were allowed to adhere for 4 hours, after which the stoppers were removed. Cells were washed one time with PBS and fully supplemented media, with or without compound, was added to the wells. After 18 hours, cells were stained with calcein AM (0.5 μg/mL) (Invitrogen, CA) and the cells that migrated to the center of the well were imaged using a Nikon microscope (Eclipse T-100); images were acquired with the CCD Sensicam mounted on a Nikon microscope (Cooke Company, MI). The detection of the cells that migrated into the previously restricted region was possible due to the addition of a detection mask at the bottom of the plate, which obstructed from measurement cells that did not migrate.

Wound Healing Assay. Breast cancer cells MDA-MB-231 are not suitable for the RT-CIM type experiments due to their thin elongated phenotype, thus the inhibition of migration was investigated using a wound healing type assay. This assay was performed using the Oris Pro Migration assay (Platypus Technologies, CMA 1.101). Briefly, 25,000 cells/well in full media were added to the 96 well plate containing stoppers to block migration of cells to the center region of the wells. Cells were allowed to adhere for 4 hours, after which the stoppers were removed. Cells were washed one time with PBS and fully supplemented media, with or without compound, was added to the wells. After 18 hours, cells were stained with calcein AM (0.5 μg/mL) (Invitrogen, CA) and the cells that migrated to the center of the well were imaged using a Nikon microscope (Eclipse T-100); images were acquired with a CCD Sensicam mounted on a Nikon microscope (PCO-TECH, Inc., Romulus, MI). The detection of the cells that migrated into the previously restricted region was possible due to the addition of a detection mask at the bottom of the plate, which obstructed from measurement cells that did not migrate.

Adhesion Assays. Similar to the migration assays, the inhibition activity of the peptide in cellular adhesion was assessed using the RT-CIM technology. In this case, 25,000 cells/well were plated in 16 wells E-plates (Roche, Basel Switzerland) in the presence or absence of the peptide. The adhesion was monitored over time (3 hours) by measuring changes in the electrical impedance, which is a direct measure of the cells adhering on the electrodes. Assays were performed in at least two independent replicates and each replicate was performed using two experimental duplicates.

Tube Formation Inhibition Assays. The compositions also were tested for their ability to inhibit tube formation, a process critical in angiogenesis. Endothelial cells spontaneously form a network of tubes when plated on extracts of extracellular matrix. This in vitro assay combines aspects of adhesion and migration and it is routinely used in angiogenesis research (Oliveira-Ferrer et al., 2008). The ability to inhibit tube formation is a comprehensive assessment of the anti-angiogenic potential. The protocol was described by Arnaoutova et al. (2009) and it consists of plating HUVEC on top of basement membrane extract. After incubation at 37° C., the cells naturally rearrange themselves in a network of tubes. Thus, 50 μL/well of Matrigel (BD Biosciences, San Jose, CA) was plated in a cold 96 well plate and incubated at 37° C. for 30 min for polymerization. 15,000 cells/well were added to the top of the gel and incubated in complete media in the presence or absence of peptide for 19 hours. Images were captured using the CCD Sensicam mounted on a Nikon microscope (Eclipse T-100). Assays were performed in at least two independent replicates and each replicate was performed using three experimental replicates and one image of a randomly chosen field was acquired per well.

Tumor Xenografts. Orthotopic breast tumors were initiated in SCID mice using human triple-negative breast cancer cells MDA-MB-231. $2\times10^6$ cells per 100 μL aliquot of single cell suspension were injected in the breast mammary fat pad. Tumors reached volumes of 75-100 mm$^3$ in approximately 14-21 days. Mice were randomized and arranged in groups (8 mice per group) with similar tumor volumes (no statistical difference among averages) and treatment was commenced. The peptide was administered once per day intraperitoneally (i.p.) at a dose of 10 mg/kg. Tumors were measured every fourth day using calipers and the tumor volume was calculated using the formula $V=ab^2/2$, where "a" is the larger and "b" is the smaller diameter.

TCM-induced metastasis model. Before tumor inoculation, athymic nude mice (female 5-6 weeks, 18-20 g) were treated with 50 μL TCM or SFM subcutaneously through the scruff for 2 weeks. After 2 weeks of TCM treatment, MDA-MB-231-luc-D3H2LN tumor xenografts were established in the same animals; the cells ($2\times10^6$) were mixed with 50 μL complete media (RPMI-1640 supplemented with 10% FBS), and 50 μL Matrigel (High Concentrated, BD Biosciences) and injected into the upper inguinal mammary fat pad of the animals under anesthesia (50 mg/kg ketamine+5 mg/kg acepromazine in PBS, 50 μL/animal, intraperitoneally dosed). The primary tumor size was measured by using a caliper, and the volume w calculated, using the formula: $V=0.52\times a\times b^2$, where 'a' is the long axis, and 'b' is the short axis of the tumor. Animals were also imaged every week to track anterior tumor metastases, using the IVIS Xenogen 200 optical imager (Xenogen, Alameda, CA) after intraperitoneal injection of d-luciferin (Caliper 150 mg/kg). 100 μL D-luciferin (twice diluted) was intraperitoneally dosed on both sides of the abdomen (total 200 μL/animals) to prevent i.p. injection failure. After 4 weeks, the axillary and brachial LN (lymph nodes), the lungs, and the brain were harvested and bathed in D-luciferin solution for 3 min and placed in the IVIS imager to detect metastases ex vivo.

Luciferase-mediated photon flux was quantified by using Living Image® 3D Analysis (Xenogen), and the average photon flux was obtained from eight lungs, eight brains, and 14-16 LNs as described before. In case of animals showing intra-abdominal metastases, ex vivo images of abdominal organs, including stomach, spleen, kidney, liver, and intestine, were obtained using the IVIS imager.

Mouse model of choroidal neovascularization (CNV). Laser photocoagulation-induced rupture of Bruch's membrane was used to generate CNV. Briefly, 4-5 week old female C57BL/6J mice were anesthetized with xylazine hydrochloride (10 mg/kg) and ketamine hydrochloride (50 mg/kg) and the pupils were dilated with 1% tropicamide (Alcon Labs, Inc., Forth Worth, TX, USA). Three burns of 532-nm diode laser photocoagulation (75 µm spot size, 0.1 s duration, 120 mW) were delivered to each retina using the slit lamp delivery system of an OcuLight GL Photocoagulator (Index, Mountain View, CA, USA) and a hand-held cover slide as a contact lens. Burns were performed in the 9, 12 and 3 o'clock positions of the posterior pole of the retina. Production of a bubble at the time of laser photocoagulation, which indicates rupture of Bruch's membrane, is an important factor in obtaining CNV, so only burns in which a bubble was produced were included in the study. Treatments were begun seven days after laser photocoagulation and included intravitreous injections of 0.1% of SP2043 (SEQ ID NO: 1) (1 µg in a volume of 1 µL), 1% (10 µg in a volume of 1 µL of SP2043 (SEQ ID NO: 1)) or vehicle under a dissecting microscope with a Harvard Pump Microinjection System (Harvard Apparatus, Holliston, MA) and pulled glass micropipettes. Some mice were euthanized for baseline measurement. Fourteen days after laser, the remaining mice were used to measure the amount of CNV at Bruch's membrane rupture sites. Two weeks after rupture of Bruch's membrane, mice were anesthetized and perfused with fluorescein-labeled dextran ($2 \times 10^6$ average mol wt, Sigma-Aldrich, St. Louis, MO, USA) and choroidal flat mounts were prepared as described previously. Briefly, the eyes were removed, fixed for 1 h in 10% phosphate-buffered formalin, and the cornea and lens were removed. The entire retina was carefully dissected from the eyecup, and then radial cuts were made from the edge of the eyecup to the equator in all four quadrants and flat-mounted in Aquamount (Polysciences, Warrington, PA). Flat mounts were examined by fluorescence microscopy using an Axioskop microscope (Zeiss, Thornwood, NY, USA) and images were digitized using a 3 CCD color video camera (IK-TU40A, Toshiba, Tokyo, Japan) and a frame grabber. Image-Pro Plus software (Media Cybernetics, Silver Spring, MD, USA) was used to measure the area of each CNV lesion. Statistical comparisons were made using ANOVA and Bonferroni.

CNV regression model. Bruch's membranes of both eyes of C57BL/6J mice were ruptured with a laser after anesthetizing the mice and dilating their pupils with 1% tropicamide. Seven days later, some mice were sacrificed to establish baseline neovascularization. At that time, 1 µg of SP2043 (SEQ ID NO: 1) was administered in one eye and vehicle in the fellow eye of other mice. Seven days later, all animals were perfused with fluorescein-labeled dextran, eyes removed, the retina dissected and flatmounted after making radial cuts, and fluorescence was measured. The images were digitized using a 3-color charge-coupled device video camera and a frame grabber and the area of hypervascularization was quantified by image-analysis software.

Transgenic mice with VEGF-induced neovascularization. At postnatal day 14, hemizygous rho/VEGF mice were given an intraocular injection of 1 µL of 5% DMSO/water, 1 µL of 5% DMSO/water containing 0.1 µg or 1 µg of SP2043 (SEQ ID No: 1) in one eye. Intraocular injections were done under a dissecting microscope with a Harvard Pump Microinjection System (Harvard Apparatus, Holliston, MA) and pulled glass micropipettes. At postnatal day 21, the total area of subretinal neovascularization (NV) per eye was quantified. Briefly, mice were anesthetized and perfused with 1 mL of PBS containing 25 mg/mL of fluorescein-labeled dextran (average molecular weight of $2 \times 10^6$, Sigma-Aldrich, St. Louis, MO). The eyes were removed and fixed for 1 hour in 10% phosphate-buffered formalin. The cornea and lens were removed, and the entire retina was carefully dissected from the eyecup, radially cut from the edge of the retina to the equator in all 4 quadrants, and flat-mounted in mounting medium (Aquamount; Polysciences, Warrington, PA) with photoreceptors facing upward. The retinas were examined by fluorescence microscopy at 200× magnification, which provides a narrow depth of field so that when focusing on NV on the outer surface of the retina, the remainder of the retinal vessels are out of focus, allowing easy delineation of the NV. The outer edge of the retina, which corresponds to the subretinal space in vivo, is easily identified and therefore there is standardization of focal plane from slide to slide. Images were digitized using a 3 charged-coupled device (CCD) color video camera and a frame grabber. By using Image analysis software (Image-Pro Plus; Media Cybernetics, Silver Spring, MD), an investigator masked with respect to treatment group allowed the software to recognize and calculated the total area of subretinal NV per eye as previously described.

Vascular permeability in mouse eyes: Mice were injected intravitreally with 1 µg of SP2043 (SEQ ID NO: 1) in one eye, and vehicle in the fellow eye and vehicle control was injected in the other eye of adult double transgenic Tet/Opsin/VEGF mice. Three days later, the mice were given 2 mg/mL doxycycline in the drinking water for 3 days. At that time the animals were anesthetized and their pupils dilated as for standard fundoscopy. The eyes were examined to compare the number of animals that had retinal detachments under the two treatments by fundus imaging using Micron II retinal imaging and optical coherence tomography imaging using published protocols.

Vascular permeability measurement in rabbit eyes: At day 0, the SP2043 peptide (SEQ ID NO:1; 50 µg) was injected into the vitreous of Dutch-belted pigmented rabbit and vehicle was injected into the fellow eye. On day 3, 50 µg of VEGF (human) was injected into both eyes. On day 10, fluorescein was injected systemically into the rabbits and 2 h later the fluorescence 5 mm to 8 mm in front of the retina was measured by a Fluoroton Master FM-2 ocular flouorophotomoter.

Materials for peptide formulations: PLGA [poly(D,L-lactide-co-glycolide); three formulations—lactide:glycolide (65:35), MW 40,000-75,000; lactide:glycolide (72:25), MW 76,000-115,000; lactide:glycolide (85:15), MW 190,000-240,000], DCM [dichloromethane], DMSO [dimethylsulfoxide], and DMF [N,N-dimethylformamide] were purchased from Sigma (St. Louis, MO). PVA [poly(vinyl alcohol); Mw 25,000] was purchased from Polysciences (Warrington, PA). PLGA-PEG [methoxy poly(ethylene glycol)-b-poly(lactide-co-glycolide); PEG:PLGA 5:20 kDa; 1:1 LA:GA) was purchased from PolySciTech (West Lafayette, IN). PBAEs [Poly(beta-amino ester)s] were synthesized as previously described. NaAc buffer (pH=5) [sodium acetate buffer] was purchased from Invitrogen (Grand Island, NY). PLGA microparticles loaded with peptide: PLGA was first dissolved into DCM, at desired concentration (usually 20 mg/mL or 40 mg/mL), in a test tube and vortexed to fully dissolve. Peptide stock in DMSO (usually 20 mg/mL) was micropipetted to the PLGA/DCM solution. The mass ratio of peptide to PLGA can vary; a common formulation is 1:50 peptide:PLGA. For blank microparticle, pipette equivalent volume of DMSO only was used. The mixture was sonicated with the test tube on ice. Sonication was performed with an amplitude setting of '30', which equaled approximately 5-10 W, for 20 seconds. This primary emulsion was immediately poured into 50 mL of 1% PVA solution and homogenized at 3.6-3.8 krpm for 1 minute. The full volume was then transferred to 100 mL of 0.5% PVA solution and stirred in a chemical hood for 3 hours. Three wash steps were performed. For each wash step, the microparticle solution was centrifuged at 4° C., 4 krpm, for 5 minutes, and then the supernatant was removed. Subsequently, 40 mL of refrigerated water was added, the microparticle pellet was resuspended and the washing steps were repeated. After the last centrifugation step, 5 mL of water was added to resuspend the sample. Samples were snap frozen in liquid nitrogen and immediately placed in a lyophilizer. Following lyophilization, all microparticles were stored at −20° C.

PLGA nanoparticles loaded with peptide: PLGA was first dissolved into DCM, at desired concentration (usually 20 mg/mL or 40 mg/mL), in a test tube and vortexed to fully dissolve. Peptide stock in DMSO (usually 20 m/mL) was micropipetted to the PLGA/DCM solution. The mass ratio of peptide to PLGA can vary; a common formulation is 1:50 peptide:PLGA. For blank nanoparticle, pipetted equivalent volume of DMSO only was used. The mixture was sonicated with the test tube on ice. Sonication was performed with an amplitude setting of '30', which equals approximately 5-10 W, for 20 seconds. This primary emulsion was immediately poured into 50 mL of 1% PVA solution and sonicated at an amplitude setting of '60' for 2 minutes. The full volume was then transferred to 100 mL of 0.5% PVA solution and stirred in a chemical hood for 3 hours. Three wash steps were performed. For each wash step, the microparticle solution was centrifuged at 4° C., 17 krpm, for 10 minutes, and then the supernatant was removed. Subsequently, 30 mL of refrigerated water was added, the microparticle pellet was resuspended and the washing steps were repeated. After the last centrifugation step, 5 mL of water was added to resuspend the sample. Samples were snap frozen in liquid nitrogen and immediately placed in a lyophilizer. Following lyophilization, all microparticles were stored at −20° C.

PLGA-PEG nanoparticles loaded with peptide: PLGA-PEG, PLGA-PEG-maleimide, or PLGA-PEG-conjugated to a ligand was first dissolved in DMF at 10 mg/mL (or other desired concentration). Then peptide (2043, 2043-IRD800; stocks at 20 mg/mL in DMF) was added to PLGA-PEG for final peptide w/w % of 2% (or other desired ratio). For blank nanoparticles, an equivalent volume of DMF only was added to PLGA-PEG. The PLGA-PEG/peptide/DMF solution was added dropwise to Milli-Q water spinning on a stir plate for a final volume ratio of organic:aqueous at 1:10. The mixture was spun under a chemical hood for 4 hours. Particles were washed twice using Amicon Ultra-15 centrifuge tubes (Millipore) at 4° C., for 10 min each spin. Concentrated particles were stored either in water at 4° C., or lyophilized with different amounts of sucrose (Sigma-Aldrich).

Polymer-peptide complexes: Each type of polymer (PBAEs) and peptide (SP2043; SEQ ID NO:1) was diluted in NaAc buffer at varying concentrations depending on desired PBAE:2043 mass ratios (from 1:1 to 100:1). The PBAE solution was pipetted to the 2043 solution and incubated at room temperature for 5 minutes. Particles were characterized by Nanosight Nanoparticle Tracking Analysis, Dynamic Light Scattering, and/or Transmission Electron Microscopy.

PLGA and PLGA-PEG particle characterization: For sizing, microparticles or nanoparticles were first diluted to 1 mg/mL in water or PBS and then sized by DLS, NTA, SEM, or TEM using appropriate. For loading, particles were first dissolved in DMSO. For part of sample, the DMSO sample was added to a larger aqueous volume to precipitate the PLGA. For labeled peptide, a Biotek Synergy 2 plate reader was used to measure fluorescence of the samples and of a labeled peptide only standard. For non-labeled 2043 samples, PAGE and silver staining were used to quantify peptide.

SEM imaging of microparticles and ImageJ quantification: Lyophilized particles were placed on carbon tape (Electron Microscopy Sciences, Hatfield, PA) and placed on aluminum mounts. Samples were sputtered with gold-palladium, and SEM imaging was performed with a LEO/Zeiss FESEM (Johns Hopkins School of Medicine).

Example 2

SP2043 Peptide (SEQ ID NO:1

The SP2043 peptide (SEQ ID NO:1) was found to inhibit the proliferation, migration, and adhesion of human umbilical vein endothelial cells (HUVEC; FIG. 1) and of retinal endothelial cells (HREC; FIG. 2). In addition, the SP2043 peptide (SEQ ID NO:1) (25 µM) was found to inhibit HUVEC tube formation (FIG. 3, Panels A and B) and microvascular endothelial cell (MEC) tube formation (FIG. 3, Panels C and D). Further, the SP2043 peptide (SEQ ID NO:1) was found to inhibit lymphatic endothelial cell adhesion (LEC; FIG. 4) and LEC tube formation (FIG. 5).

The SP2043 peptide (SEQ ID NO:1) also was found to inhibit hepatocyte growth factor (HGF) and insulin growth factor 1 (IGF1) signaling in vitro in MEC and LEC cells (FIG. 6). In addition, the SP2043 peptide (SEQ ID NO:1) was found to inhibit the proliferation of triple-negative breast cancer cell lines MDA-MB-231 and SUM149 as well as the estrogen receptor positive cell line MCF-7 in vitro (FIG. 7). Further, the SP2043 peptide (SEQ ID NO:1) was found to inhibit HGF signaling in MDA-MB-231 cells (FIG. 8).

The SP2043 peptide (SEQ ID NO:1) also showed inhibition in vivo by inhibiting the growth of MDA-MB-231 orthotopic tumors in SCID mice (FIG. 9). 33 days after the injection of the SP2043 peptide (SEQ ID NO:1) into the mice, the growth of the tumors was inhibited about 82% (using 20 mg of SP2043/kg with an intraperitoneal injection). The SP2043 peptide (SEQ ID NO:1) also was found to inhibit phosphorylation of c-Met and angiogenesis in vivo (FIG. 10). The SP2043 peptide (SEQ ID NO:1) inhibited angiogenesis as seen by lectin staining for immunohistochemistry (IHC) and lymphangiogenesis as seen by LYVE-1 staining in vivo (FIG. 11). SP2043 inhibited metastasis of MDA-MB-231-luc tumors to multiple organs in the tumor-conditioned media pre-treated metastasis model by photon flux from tumor cells (FIG. 12A). The SP2043 peptide (SEQ ID NO:1) also inhibited metastasis of MDA-MB-231-luc tumors to lymph nodes as seen by staining with vimentin antibody for the presence of human cells (FIG. 12B).

Figure 13A:
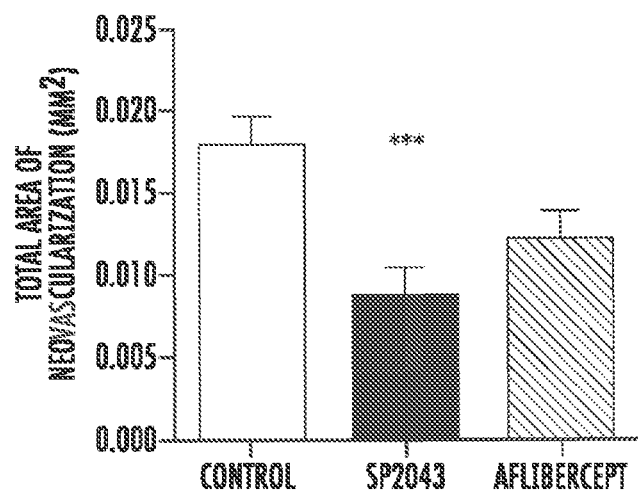
Figure 13B:
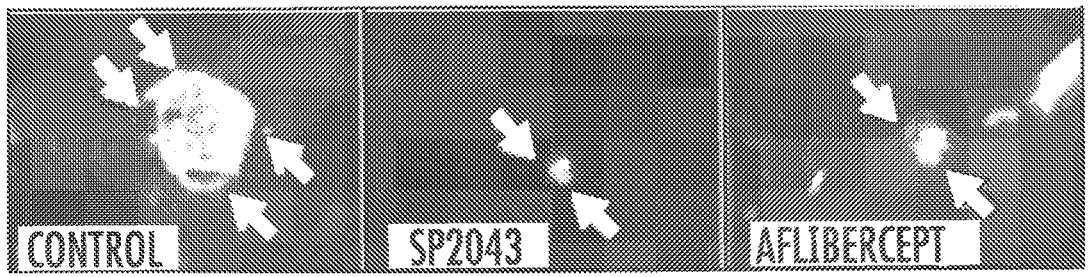
Figure 13C:
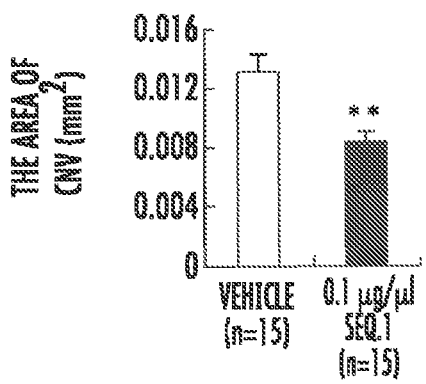
Figure 13D:
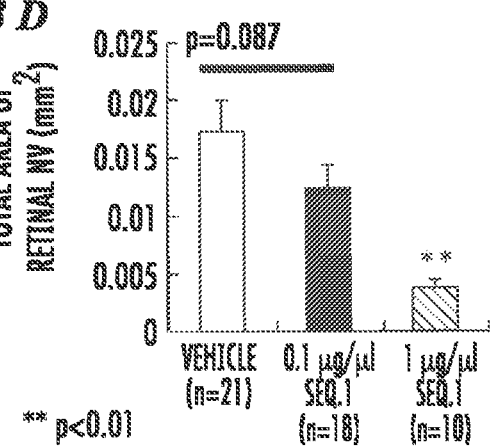
Figure 13E:
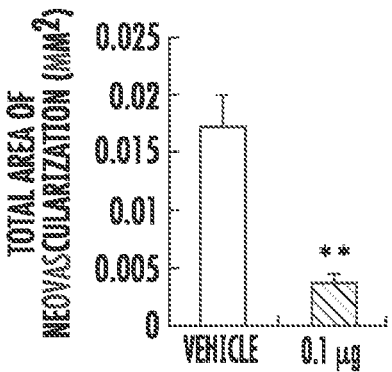

The effect of the SP2043 peptide (SEQ ID NO:1) was also seen in ocular models of human ocular diseases such as age-related macular degeneration (AMD), macular edema (ME) and diabetic macular edema (DME). The SP2043 peptide (SEQ ID NO:1) inhibited neovascularization in a laser induced choroidal neovascularization (CNV) model more potently than aflibercept (FIGS. 13A-B), as well as in a rho-VEGF mouse model compared to a control (FIGS. 13C-E). In addition, the SP2043 peptide (SEQ ID NO:1) caused regression of the neovasculature in a laser induced CNV model in the mouse eye (FIG. 14). Further, the SP2043 peptide (SEQ ID NO:1) inhibited vascular leakage in the Tet/Opsin/VEGF mouse model (FIGS. 15A-B). Also, the SP2043 peptide (SEQ ID NO:1) inhibited VEGF mediated vascular permeability in the rabbit eye (FIG. 16).

Example 3

SP2043 Peptide (SEQ ID NO:1) in Microparticles

The presently disclosed isolated peptides can be formulated and used in microparticles or nanoparticles. The SP2043 peptide (SEQ ID NO:1) was formulated into PLGA microparticles to enable long-term sustained release and shown by scanning electron microscope (SEM) imaging (2% loaded; FIG. 17). FIG. 18A shows a representative example of the sizing of 2% and 5% SP2043 loaded PLGA microparticles. The sizing of the microparticles was measured with ImageJ (Rasband, 1997-2012) of SEM images. Results showed that loading with the SP2043 peptide (SEQ ID NO:1) does not significantly affect the particle size distribution. In some embodiments, about 2% to 5% peptide loaded PLGA is used in the presently disclosed methods. For in vivo use, 5% by mass SP2043 peptide (SEQ ID NO:1) is equivalent to 1 µg SP2043 peptide (SEQ ID NO:1) in 1 µL of injected microparticle solution. The zeta potentials (surface charge) of 2% and 5% SP2043 peptide (SEQ ID NO:1) loaded microparticles were measured on a Malvern Zetasizer (Malvern Instruments, Ltd, Malvern, Worcestershire, UK; FIG. 18B). The results showed no significant difference in surface charge between the control (blank) and the peptide loaded microparticles.

Controlled release of a labeled peptide analog of SP2043 peptide (SEQ ID NO:1) from PLGA microparticles was observed over six months under physiological conditions in situ (PBS at 37° C.; FIG. 19A and FIG. 19B). In addition, the controlled release of the SP2043 peptide (SEQ ID NO:1) without any label or modification in PLGA microparticles in situ under physiological conditions also was observed (FIG. 20).

FIG. 21 shows SEM imaging of PLGA microparticles incorporating 2% by weight of SP2043 peptide (SEQ ID NO:1) (left) and 5% by weight 2043 (right). The SP2043 peptide (SEQ ID NO:1) can also be encapsulated into nanoparticles and these particles (micro or nano) can have different non-spherical shapes, such as ellipsoidal and spherical shapes (FIG. 22).

The PLGA 85/15 microparticle encapsulating the SP2043 peptide (SEQ ID NO:1) caused regression in mouse eyes following laser-induced choroidal neovascularization in a mouse model (FIG. 23). In addition, these microparticles inhibited neovascularization overtime in a laser-induced wet AMD mouse model (FIG. 24). PLGA 85/15 microparticles encapsulating 2043 showed efficacy for at least 3 month in vivo following a single intravitreal injection.

The PLGA 65/35 microparticles containing the SP2043 peptide (SEQ ID NO:1) inhibited neovascularization overtime in a laser-induced wet AMD mouse model (FIG. 25). Inhibition of neovascularization by the SP2043 peptide (SEQ ID NO:1) was also seen in a rabbit model (FIG. 26).

FIG. 27 shows PLGA (85/15) encapsulating the SP2043 peptide (SEQ ID NO:1) in rho/VEGF transgenic mice. FIG. 28 shows that the SP2043 peptide (SEQ ID NO:1) can be used in combination with other anti-angiogenesis agents, such as aflibercept, for increased effect as seen in a laser-induced choroidal neovascularization model in mice.

Polymers, such as PBAEs, can be added to SP2043 to self-assemble it into approximately 100 nm nanoparticles (FIG. 29). Particle size and nanoparticle concentration were found to be larger when the SP2043 peptide (SEQ ID NO:1) was together with a polymer for self-assembly. FIG. 30 shows the effect of PLGA and PLGA-PEG nanoparticles encapsulating the SP2043 peptide (SEQ ID NO:1).

Systemically intravenous injected SP2043 peptide (SEQ ID NO:1) containing nanoparticles or free peptide accumulated in tumor as well as other organs (FIG. 31).

The method for quantifying the SP2043 peptide (SEQ ID NO:1) comprised electrophoresis and staining with SimplyBlue (FIG. 32, Panel A), followed by mass spectrometry (FIG. 32, Panel B).

Example 4

Discussion

The presently disclosed subject matter provides mimetic peptides that can be used for different forms of cancer, ocular diseases, such as age-related macular degeneration, and other angiogenesis-dependent and lymphangiogenesis-dependent diseases. In particular, the active mimetic peptide SP2043 (SEQ ID NO: 1) was tested in angiogenesis and lymphangiogenesis assays in vitro. More particularly, the SP2043 peptide (SEQ ID NO:1) demonstrated anti-angiogenic activity in blood endothelial cell proliferation, migration, adhesion, and tube formation assays, and anti-angiogenic and anti-tumorigenic activity in vivo in breast cancer xenograft models, and age-related macular degeneration models. The SP2043 peptide (SEQ ID NO:1) also has anti-lymphangiogenic properties. In addition, it was shown that the SP2043 peptide (SEQ ID NO:1) can be formulated and used in microparticles or nanoparticles.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Abraham S, Guo F, Li L S, Rader C, Liu C, Barbas C F, 3rd, et al. (2007) Synthesis of the next generation therapeutic antibodies that combine cell targeting and antibody-catalyzed prodrug activation. *Proc Natl Acad Sci USA;*104: 5584-9.

Amaoutova I, George J, Kleinman H K, Benton G (2009) The endothelial cell tube formation assay on basement membrane turns 20: state of the science and the art. *Angiogenesis;*12: 267-74.

Avraamides, C. J.; Garmy-Susini, B.; Varner, J. A. Integrins in angiogenesis and lymphangiogenesis. *Nat. Rev. Cancer,* 2008, 8(8), 604-617.

Bhujwalla Z M, Artemov D, Natarajan K, Ackerstaff E, Solaiyappan M. Vascular differences detected by MRI for metastatic versus nonmetastatic breast and prostate cancer xenografts. Neoplasia 2001; 3:143-53.

Bhutia, S. K.; Maiti, T. K. Targeting tumors with peptides from natural sources. *Trends Biotechnol.,* 2008, 26(4), 210-217.

Bradley, D. A.; Daignault, S.; Ryan, C. J.; Dipaola, R. S.; Smith, D. C.; Small, E.; Gross, M. E.; Stein, M. N.; Chen, A.; Hussain, M. Cilengitide (EMD 121974, NSC 707544) in asymptomatic metastatic castration resistant prostate cancer patients: a randomized phase II trial by the prostate cancer clinical trials consortium. *Invest. New Drugs.*

Carmeliet, P. Angiogenesis in life, disease and medicine. *Nature,* 2005, 438(7070), 932-936.

Carmeliet, P.; Jain, R. K. Angiogenesis in cancer and other diseases. *Nature,* 2000, 407(6801), 249-257.

Carmeliet P, Jain R K. Molecular mechanisms and clinical applications of angiogenesis. Nature. 2011 May 19;473 (7347):298-307.

Eikesdal, H. P.; Sugimoto, H.; Birrane, G.; Maeshima, Y.; Cooke, V. G.; Kieran, M.; Kalluri, R. Identification of amino acids essential for the antiangiogenic activity of tumstatin and its use in combination antitumor activity. *Proc. Natl. Acad. Sci. USA,* 2008, 105(39), 15040-15045.

Elkin M and Vlodaysky I. Tail vein assay of cancer metastasis. *Curr Protoc Cell Biol Chapter* 19: Unit 19 12, 2001.

Folkman, J. Tumor angiogenesis: therapeutic implications. *N. Engl. J.Med.,* 1971, 285(21), 1182-1186.

Folkman J (2002) Role of angiogenesis in tumor growth and metastasis. *Semin Oncol;*29: 15-8.

Folkman, J., Angiogenesis. *Annu. Rev. Med.,* 2006, 57, 1-18.

Gautier B, Goncalves V, Diana D, Di Stasi R, Teillet F, Lenoir C, et al. (2010) Biochemical and structural analysis of the binding determinants of a vascular endothelial growth factor receptor peptidic antagonist. *J Med Chem;* 53: 4428-40.

Gentilucci L, De Marco R, Cerisoli L (2010) Chemical modifications designed to improve peptide stability: incorporation of non-natural amino acids, pseudo-peptide bonds, and cyclization. *Curr Pharm Des;*16: 3185-203.

Haviv, F.; Bradley, M. F.; Kalvin, D. M.; Schneider, A. J.; Davidson, D. J.; Majest, S. M.; McKay, L. M.; Haskell, C. J.; Bell, R. L.; Nguyen, B.; Marsh, K. C.; Surber, B. W.; Uchic, J. T.; Ferrero, J.; Wang, Y. C.; Leal, J.; Record, R. D.; Hodde, J.; Badylak, S. F.; Lesniewski, R. R.; Henkin, J. Thrombospondin-1 mimetic peptide inhibitors of angiogenesis and tumor growth: design, synthesis, and optimization of pharmacokinetics and biological activities. *J. Med. Chem.,* 2005, 48(8), 2838-2846.

Holopainen T, Bry M, Alitalo K, Saaristo A. Perspectives on lymphangiogenesis and angiogenesis in cancer. J Surg Oncol. 2011 May 1;103(6):484-8.Hruby V J, Sharma S D, Toth K, Jaw J Y, al-Obeidi F, Sawyer T K, et al. (1993) Design, synthesis, and conformation of superpotent and prolonged acting melanotropins. *Ann N Y Acad Sci;* 680: 51-63.

Karagiannis, E. D.; Popel, A. S. Identification of novel short peptides derived from the alpha 4, alpha 5, and alpha 6 fibrils of type IV collagen with anti-angiogenic properties. *Biochem. Biophys. Res. Commun.,* 2007, 354(2), 434-439.

Karagiannis E D, Popel A S. A systematic methodology for proteome-wide identification of peptides inhibiting the proliferation and migration of endothelial cells. Proc Natl Acad Sci U.S.A. 2008 Sep. 16;105(37):13775-80.

Kenny, L. M.; Coombes, R. C.; Oulie, I.; Contractor, K. B.; Miller, M.; Spinks, T. J.; McParland, B.; Cohen, P. S.; Hui, A. M.; Palmieri, C.; Osman, S.; Glaser, M.; Turton, D.; Al-Nahhas, A.; Aboagye, E. O. Phase I trial of the positron-emitting Arg-Gly-Asp (RGD) peptide radioligand 18F-AH111585 in breast cancer patients. *J. Nucl.Med.,* 2008, 49(6), 879-886.

Koskimaki, J. E.; Karagiannis, E. D.; Rosca, E. V.; Vesuna, F.; Winnard, P. T. Jr.; Raman, V.; Bhujwalla, Z. M.; Popel, A. S., Peptides derived from type IV collagen, CXC chemokines, and thrombospondin-1 domain-containing proteins inhibit neovascularization and suppress tumor growth in MDA-MB-231 breast cancer xenografts. *Neoplasia,* 2009, 11(12), 1285-1291.

Koskimaki, J. E.; Karagiannis, E. D.; Tang, B. C.; Hammers, H.; Watkins, D. N.; Pili, R.; Popel, A. S. Pentastatin-1, a collagen IV derived 20-mer peptide, suppresses tumor growth in a small cell lung cancer xenograft model. *BMC Cancer,* 2010, 10, 29.

Lee E, Rosca E V, Pandey N B, Popel A S (2011) Small peptides derived from somatotropin conserved domain-containing proteins inhibit blood and lymphatic endothelial cell proliferation, migration, adhesion and tube formation. *Int J Biochem Cell Biol,* 2011, 43(12):1812-1821;

Leung, D. W.; Cachianes, G.; Kuang, W. J.; Goeddel, D. V.; Ferrara, N. Vascular endothelial growth factor is a secreted angiogenic mitogen. *Science,* 1989, 246(4935), 1306-1309.

Li M, Oliver E, Kitchens K M, Vere J, Alkan S S, Tamiz A P (2008) Structure-activity relationship studies of permeability modulating peptide AT-1002. *Bioorg Med Chem Lett;* 18: 4584-6.

Ma J. S., Unnatural amino acids in drug discovery. CHIMICA OGGI chemistry today, 2003, 65-68.Mirochnik, Y.; Aurora, A.; Schulze-Hoepfner, F. T.; Deabes, A.; Shifrin, V.; Beckmann, R.; Polsky, C.; Volpert, O. V. Short pigment epithelial-derived factor-derived peptide inhibits angiogenesis and tumor growth. *Clin. Cancer Res.,* 2009, 15(5), 1655-1663.

Nabors, L. B.; Fiveash, J. B.; Markert, J. M.; Kekan, M. S.; Gillespie, G. Y.; Huang, Z.; Johnson, M. J.; Meleth, S.; Kuo, H.; Gladson, C. L.; Fathallah-Shaykh, H. M. A phase 1 trial of ABT-510 concurrent with standard chemoradiation for patients with newly diagnosed glioblastoma. *Arch. Neural.,* 67(3), 313-319.

Ogan M D, Schmiedl U, Moseley M E, Grodd W, Paajanen H, Brasch R C., Albumin labeled with Gd-DTPA. An intravascular contrast-enhancing agent for magnetic resonance blood pool imaging: preparation and characterization. Invest Radiol. 1988 Dec;23(12):961.

Okamoto N, Tobe T, Hackett S F, Ozaki H, Vinores M A, LaRochelle W, Zack D J, Campochiaro P A: Transgenic mice with increased expression of vascular endothelial growth factor in the retina: a new model of intraretinal and subretinal neovascularization, Am. J. Pathol. 1997, 151: 281-291.

Perrot M, Vanderesse R, Frochot C, Guillemin F, Barberi-Heyob M (2011) Stability of peptides and therapeutic success in cancer. *Expert Opin Drug Metab Toxicol;* 7: 793-802.

Raman V, Artemov D, Pathak A P, Winnard Jr P T, McNutt S, Yudina A, Bogdanov Jr A, Bhujwalla Z M. Characterizing vascular parameters in hypoxic regions: A combined magnetic resonance and optical imaging study of a human prostate cancer model. Cancer Res 2006; 66:9929-36.

Rasband, W. S., ImageJ, U. S. National Institutes of Health, Bethesda, Maryland, USA, the World Wide Web (www) at imagej.nih.gov/ij/, 1997-2012.

Reardon, D. A.; Fink, K. L.; Mikkelsen, T.; Cloughesy, T. F.; O'Neill, A.; Plotkin, S.; Glantz, M.; Ravin, P.; Raizer, J. J.; Rich, K. M.; Schiff, D.; Shapiro, W. R.; Burdette-Radoux, S.; Dropcho, E. J.; Wittemer, S. M.; Nippgen, J.; Picard, M.; Nabors, L. B. Randomized phase II study of cilengitide, an integrin-targeting arginine-glycine-aspartic acid peptide, in recurrent glioblastoma multiforme. *J. Clin. Oncol.,* 2008, 26(34), 5610-5617.

Reichert, J. Development trends for peptide therapeutics *Periodical* [Online], 2008, p. the World Wide Web (www) at peptidetherapeutics.org/PTF_Summary_2008.pdf.

Rivera C G, Rosca E V, Pandey N B, Koskimaki J E, Bader J S, Popel A S (2011) Novel peptide specific (QSAR) analysis applied to collagen IV peptides with antiangiogenic activity. *J Med Chem,* 54(19):6492-500 (2011).

Rosca E V, Koskimaki J E, Pandey N B, Rivera C G, Tamiz A P, Popel A S (2011) Anti-angiogenic peptides for cancer therapeutics. *Current Pharmaceutical Biotechnology;* 12: 1101-16.

Rosca E V, Koskimaki J E, Pandey N B, Wolff A C, Popel A S (2011) Development of a biomimetic peptide derived from collagen IV with anti-angiogenic activity in breast cancer. *CancerBiology & Therapy;* 12:808-17.

Saladin, P. M.; Zhang, B. D.; Reichert, J. M. Current trends in the clinical development of peptide therapeutics. *IDrugs,* 2009, 12(12), 779-784.

Senger, D. R.; Galli, S. J.; Dvorak, A. M.; Perruzzi, C. A.; Harvey, V. S.; Dvorak, H. F. Tumor cells secrete a vascular permeability factor that promotes accumulation of ascites fluid. *Science,* 1983, 219(4587), 983-985.

Tobe T, Okamoto N, Vinores M A, Derevjanik N L, Vinores S A, Zack D J, Campochiaro P A: Evolution of neovascularization in mice with overexpression of vascular endothelial growth factor in photoreceptors, Invest. Ophthalmol. Vis. Sci. 1998, 39:180-188.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for treating a condition associated with angiogenesis, lymphangiogenesis, vascular permeability, or tumorigenesis, comprising administering an effective amount of a peptide comprising the amino acid sequence of LRRFSTXPXXXXDINDVXNF (SEQ ID NO: 2), wherein X is any amino acid and the amino acid sequence is at least 85% identical to LRRFSTAPFAFIDINDVINF (SEQ ID NO: 1) and wherein X at position 7 is selected from M, A, and G; X at position 9 is selected from F, A, Y, and G, X at position 10 is selected from M, A, G, dA, and Nle, X at position 11 is selected from F, A, Y, G, and 4-C1Phe, and X at position 12 and position 18 are selected from Abu, G, S, A, V, T, I, L, and AllyGly.

2. The method of claim 1, wherein the peptide is administered as a pharmaceutical composition comprising the effective amount of the peptide and a pharmaceutically acceptable carrier.

3. The method of claim 1, wherein the pharmaceutical composition is administered locally or systemically.

4. The method of claim 3, wherein the pharmaceutical composition is formulated for parenteral delivery.

5. The method of claim 1, wherein the condition is cancer.

6. The method of claim 5, wherein the cancer is cancer of the breast, lung, glioblastoma, renal cell, hepatic cell, head, or neck.

7. The method of claim 5, wherein the cancer relies on lymphangiogenesis to occur or spread.

8. The method of claim 1, wherein the condition involves ocular angiogenesis.

9. The method of claim 8, wherein the pharmaceutical composition is administered by intraocular delivery.

10. The method of claim 8, wherein the condition is selected from age-related macular degeneration, diabetic macular edema (DME), diabetic retinopathy, and macular edema (ME).

11. The method of claim 8, wherein the condition is macular edema.

12. The method of claim 8, wherein the condition is neovascular glaucoma.

13. The method of claim 8, wherein the condition is proliferative diabetic retinopathy.

14. The method of claim 8, wherein the condition is retinopathy of prematurity.

15. The method of claim 1, wherein the method treats ocular angiogenesis in or surrounding a tumor.

16. The method of claim 5, wherein the tumor is a primary tumor or an established metastasized tumor.

17. The method of claim 5, wherein the method inhibits the establishment of metastasis or inhibits further metastasis of the tumor.

18. The method of claim 5, wherein the method inhibits dissemination of tumor cells through the blood.

19. The method of claim 1, wherein the amino acid sequence is at least 90% identical to SEQ ID NO: 1.

20. The method of claim 1, wherein the amino acid sequence is at least 95% identical to SEQ ID NO: 1.

21. The method of claim 1, wherein at least one X is a natural amino acid.

22. The method of claim 1, wherein at least one X is a non-natural amino acid.

23. The method of claim 22, wherein the non-natural amino acid is selected from 2-aminobutyric acid (Abu), norleucine (Nle), 4-chloro phenylalanine (4-ClPhe), and allylglycine (AllyGly).

24. The method of claim 1, wherein X at position 7 is A.

25. The method of claim 1, wherein X at position 9 is F.

26. The method of claim 1, wherein X at position 10 is A.

27. The method of claim 1, wherein X at position 11 is F.

28. The method of claim 1, wherein X at position 7 is A, X at position 9 is F, X at position 10 is A, and X at position 11 is F.

29. The method of claim 6, wherein the peptide has the amino acid sequence of SEQ ID NO: 1.

* * * * *

SEQUENCE LISTING

```
<160> NUMBER OF SEQ ID NOS: 4

<210> SEQ ID NO 1
<211> LENGTH: 20
<212> TYPE: PRT
<213> ORGANISM: Artificial Sequence
<220> FEATURE:
<223> OTHER INFORMATION: Artificial sequence based on human Collagen
      Type IV protein

<400> SEQUENCE: 1

Leu Arg Arg Phe Ser Thr Ala Pro Phe Ala Phe Ile Asp Ile Asn Asp
1               5                   10                  15

Val Ile Asn Phe
            20

<210> SEQ ID NO 2
<211> LENGTH: 20
<212> TYPE: PRT
<213> ORGANISM: Artificial Sequence
<220> FEATURE:
<223> OTHER INFORMATION: Artificial sequence based on human Collagen
      Type IV protein
<220> FEATURE:
<221> NAME/KEY: MISC_FEATURE
<222> LOCATION: (7)..(7)
<223> OTHER INFORMATION: Xaa is any natural or non-natural amino acid
<220> FEATURE:
<221> NAME/KEY: MISC_FEATURE
<222> LOCATION: (9)..(12)
<223> OTHER INFORMATION: Xaa is any natural or non-natural amino acid
<220> FEATURE:
<221> NAME/KEY: MISC_FEATURE
<222> LOCATION: (18)..(18)
<223> OTHER INFORMATION: Xaa is any natural or non-natural amino acid

<400> SEQUENCE: 2

Leu Arg Arg Phe Ser Thr Xaa Pro Xaa Xaa Xaa Xaa Asp Ile Asn Asp
1               5                   10                  15

Val Xaa Asn Phe
            20

<210> SEQ ID NO 3
<211> LENGTH: 20
```

```
<212> TYPE: PRT
<213> ORGANISM: Artificial Sequence
<220> FEATURE:
<223> OTHER INFORMATION: Artificial sequence based on human Collagen
      Type IV protein

<400> SEQUENCE: 3

Leu Arg Arg Phe Ser Thr Ala Pro Phe Ala Phe Ile Asn Ile Asn Asn
1               5                   10                  15

Val Ile Asn Phe
            20

<210> SEQ ID NO 4
<211> LENGTH: 20
<212> TYPE: PRT
<213> ORGANISM: Artificial Sequence
<220> FEATURE:
<223> OTHER INFORMATION: Artificial sequence based on human Collagen
      Type IV protein
<220> FEATURE:
<221> NAME/KEY: MISC_FEATURE
<222> LOCATION: (7)..(7)
<223> OTHER INFORMATION: Xaa is any natural or non-natural amino acid
<220> FEATURE:
<221> NAME/KEY: MISC_FEATURE
<222> LOCATION: (9)..(12)
<223> OTHER INFORMATION: Xaa is any natural or non-natural amino acid
<220> FEATURE:
<221> NAME/KEY: MISC_FEATURE
<222> LOCATION: (18)..(18)
<223> OTHER INFORMATION: Xaa is any natural or non-natural amino acid

<400> SEQUENCE: 4

Leu Arg Arg Phe Ser Thr Xaa Pro Xaa Xaa Xaa Xaa Asn Ile Asn Asn
1               5                   10                  15

Val Xaa Asn Phe
            20
```